(12) United States Patent
Lopez et al.

(10) Patent No.: US 11,707,465 B2
(45) Date of Patent: *Jul. 25, 2023

(54) THEACRINE-BASED SUPPLEMENT AND METHOD OF USE THEREOF IN A SYNERGISTIC COMBINATION WITH CAFFEINE

(71) Applicant: Ortho-Nutra, LLC, Morganville, NJ (US)

(72) Inventors: Hector L. Lopez, Cream Ridge, NJ (US); Shawn Wells, Lewisville, TX (US); Tim N. Ziegenfuss, Chardon, OH (US)

(73) Assignee: Ortho-Nutra LLC, Morganville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/884,346

(22) Filed: Aug. 9, 2022

(65) Prior Publication Data

US 2023/0147386 A1 May 11, 2023

Related U.S. Application Data

(60) Division of application No. 16/551,373, filed on Aug. 26, 2019, now Pat. No. 11,426,410, which is a continuation of application No. 15/600,371, filed on May 19, 2017, now Pat. No. 10,398,701, which is a continuation-in-part of application No. 14/539,726, filed on Nov. 12, 2014, now Pat. No. 10,272,091.

(60) Provisional application No. 61/903,362, filed on Nov. 12, 2013.

(51) Int. Cl.
| | |
|---|---|
| A61K 31/522 | (2006.01) |
| C07D 487/04 | (2006.01) |
| A23L 33/10 | (2016.01) |
| A23L 33/105 | (2016.01) |
| A61K 31/133 | (2006.01) |
| A61K 31/14 | (2006.01) |
| A61K 31/4748 | (2006.01) |
| A61K 31/685 | (2006.01) |
| A61K 31/7048 | (2006.01) |
| A61K 31/7068 | (2006.01) |

(52) U.S. Cl.
CPC ............ *A61K 31/522* (2013.01); *A23L 33/10* (2016.08); *A23L 33/105* (2016.08); *A61K 31/133* (2013.01); *A61K 31/14* (2013.01); *A61K 31/4748* (2013.01); *A61K 31/685* (2013.01); *A61K 31/7048* (2013.01); *A61K 31/7068* (2013.01); *C07D 487/04* (2013.01); *A23V 2002/00* (2013.01)

(58) Field of Classification Search
CPC .... A61K 31/522; A61K 31/133; A61K 31/14; A61K 31/4748; A61K 31/685; A61K 31/7048; A61K 31/7068; A23L 33/10; A23L 33/105; C07D 487/04; A23V 2002/00

See application file for complete search history.

(56) References Cited

U.S. PATENT DOCUMENTS

| | | |
|---|---|---|
| 4,833,147 A | 5/1989 | Moeller et al. |
| 2015/0132280 A1 | 5/2015 | Lopez et al. |
| 2015/0238494 A1 | 8/2015 | Owoc |
| 2021/0137928 A1 | 5/2021 | Lopez et al. |

FOREIGN PATENT DOCUMENTS

| | | |
|---|---|---|
| CN | 101289448 A | 10/2008 |
| WO | 2018/112475 A1 | 6/2018 |

OTHER PUBLICATIONS

Kuhman et al, "Cognitive Performance and Mood Following Ingestion of a Theacrine-Containing Dietary Supplement, Caffeine, or Placebo by Young Men and Women", Nutrients, vol. 7, Nov. 19, 2015, pp. 9618-9632.

Wanner et al, "O(2),1,9-Trimethyluric Acid and 1,3,7,9-Tetramethyluric Acid in Leaves of Different Coffea Species" Phytochemistry, 1975, 14:747-750.

Li et al, "Antioxidative activities and the chemical constituents of two Chinese tease, Camellia kucha and C. ptilophylla", Intl. J. of Food Science and Tech, 2012, 47:1063-1071.

Feduccia et al, "Locomotor activation by theacrine, a purine alkaloid structurally similar to caffeine: Involvement of adenosine and dopamine receptors", Pharmacology, Biochemistry and Behavior, 2012, 102:241-248.

(Continued)

*Primary Examiner* — Kade Ariani
(74) *Attorney, Agent, or Firm* — Amin Talati Wasserman LLP; George M. Carrera, Jr.; Valerie Neymeyer-Tynkov

(57) ABSTRACT

A human dietary supplement comprises theacrine and optionally other compounds that modulate the effects of theacrine. Uses for the theacrine-containing supplement include improvement of at least one of mood, energy, focus, concentration or sexual desire or a reduction of at least one of anxiety or fatigue. A synergistic composition comprises co-administration of theacrine and caffeine, wherein the co-administered caffeine reduces theacrine oral clearance (CL/F) and oral volume of distribution (Vd/F). In addition, the co-administered caffeine increases area under the plasma concentration time curve (AUC) of theacrine, and increases theacrine maximum plasma concentration ($C_{max}$) in comparison with the corresponding pharmacokinetic parameters when theacrine is administered alone.

24 Claims, 18 Drawing Sheets

(56) References Cited

OTHER PUBLICATIONS

Petermann et al, "Metabolic Relations between Methylxanthines and Methyluric Acids in Coffea L.", Plant Physiol., 1983, 73:961-964.

Zheng et al, "Theacrine (1,3,7,9-tetramethyluric acid) synthesis in leaves of a Chinese tea, kucha (*Camellia assamica* var. *kucha*)", Phytochemistry, 2002, 60:129-134.

Li et al, "Theacrine, a Purine Alkaloid Obtained from Camellia assamica var. kucha, Attenuates Restraint Stress-Provoked Liver Damage in Mice", J. of Agricultural and Food Chem., 2013, 61:6328-6335.

Wang et al, "Theacrine, a purine alkaloid with anti-inflammatory and analgesic activities," Fitoterapia, 2010, 81:627-631.

Xu et al, "Theacrine, a special purine alkaloid with sedative and hypnotic properties from Cammelia assamica var. kucha in mice", J. of Asian Natural Products Research, 2007, vol. 9, No. 7, 665-672.

Xie et al., Chinese Pharmacological Bulletin, 2009, 9:13, Abstract Only.

Fisone et al., CMLS, Cell. Mol. Life Sci., 2004, vol. 61, p. 857-872.

Fox, K.R, Public Health Nutrition, 1999, vol. 2, No. 3a, p. 411-418.

Maridakis et al., International Journal of Neuroscience, 2009, vol. 119, p. 975-994.

Proceedings of the Eleventh International Society of Sports Nutrition (ISSN) Conference and Expo; Journal of the International Society of Sports Nutrition 2014, vol. 11 Suppl 1, published Dec. 1, 2014, 21 pages.

Lack of Drive? Theacrine will get you going dated May 19, 2012 and archived by the Internet Archive on Oct. 18, 2013.

Ye, Chuang-Xing, "New Discovery of Pattern of Purine Alkaloids in Wild Tea Trees," Acta Scientiarum Naturalium Universitatis Sunyatseni, Jan. 1, 2003, 42(1):62-65, Abstract only.

Theacrine Scientific Review on Usage Dosage Side Effects from Examine.com dated Nov. 20, 2013 and archived by the Internet Archive on Dec. 2, 2013.

PubChem compound summary for theobromine, downloaded on Nov. 20, 2018, 2 pages of PDF (cited in Notice of References Cited issued in parent U.S. Appl. No. 15/600,371).

PubChem compound summary for naringin, downloaded on Nov. 20, 2018, 3 pages of PDF (cited in Notice of References Cited issued in parent U.S. Appl. No. 15/600,371).

Grossman, R., Am J Clin Dermatol. 2005, vol. 6, No. 1, p. 39-47, Abstract Oonly (cited in Notice of References Cited issued in parent U.S. Appl. No. 15/600,371).

Kumar et al., Food Reviews International, 2009, vol. 25, p. 175-197 (cited in Notice of References Cited issued in parent U.S. Appl. No. 15/600,371).

Definition of synergism. (1992). In C. G. Morris (Ed.), Academic Press Dictionary of Science and Technology (4th ed.). Oxford, UK: Elsevier Sciences Technology. Retrieved from https://search.credoreference.com/content/entry/apdst/synergism/0?institutionld=743 on Nov. 21, 2018, 1 page (cited in Notice of References Cited issued in parent U.S. Appl. No. 15/600,371).

International Searching Authority of the US Patent and Trademark Office, "International Search Report and Written Opinion" issued in related foreign patent application No. PCT/US2020/058138, dated Feb. 2, 2021, pp. 1-8.

Davis, JL, "Antioxidants in Green and Black Tea," Sep. 11, 2008. Retrieved from the Internet < URL: https://webmd.com/food-recipes/features/antioxidants-in-gree-and-black-tea#1> 6 pages.

Roberts, C, "Is There More Caffeine in Espresso Than in Coffee?" Nov. 13, 2018. Retrieved from the Internet < URL: https://www.consumerreports.org/coffee/is-there-more-caffeine-in-espresso-than-in-coffee/#:~text+By%20the%20Numbers,mg%20of%20caffeine%20per%20ounce.> 7 pages.

Lu et al., "Determination of purine alkaloids and catechins in different parts of Camellia assamica var. kucha by HPLC-DAD/ESI-MS/MS," Wiley Interscience, pp. 2024-2029 (Jul. 20, 2009).

Wang, D. et al., "Primary Studies on Acute Toxicity and Sedative/Hypnotic Activity of Camellia kucha" J. Sun Yat-San Univ. 49(1):76-79 (2010).

Satoshi Ikuta "Brain Use Manual Full Color Edition" Jilin Publishing Group p. 32 (2012) (cited as "common knowledge" document).

Sun, S. et al. "Food Toxicology" Wuhan University of Technology Press p. 170-173 (2012) (cited as "common knowledge" document).

Clarke, R.J., et al., Coffee, vol. 3; Physiology, Springer Science and Business Media, Dec. 31, 1988—Technology and Engineering—388 pages, pp. 2 and 4 Only.

International Searching Authority of the US Patent and Trademark Office, "International Search Report and Written Opinion" issued in related foreign patent application No. PCT/US14/65289, dated Jan. 21, 2015, 5 pages.

U.S. Food and Drug Administration, "Science and Our Food Supply. Examining Dietary Supplements. Teacher's Guide for High School Classroom", 1st Edition, from www.fda.gov/media/152680/download, 2021, 89 pages.

Units for vertical axis are Visual Analogue Scale (in cm).

THEACRINE-BASED SUPPLEMENT AND METHOD OF USE THEREOF IN A SYNERGISTIC COMBINATION WITH CAFFEINE

This application is a divisional application claiming the benefit of U.S. patent application Ser. No. 16/551,373, filed Aug. 26, 2019, which is a continuation application claiming the benefit of U.S. patent application Ser. No. 15/600,371, filed May 19, 2017 and issued as U.S. Pat. No. 10,398,701, which is a continuation-in-part application claiming the benefit of U.S. Ser. No. 14/539,726, filed Nov. 12, 2014 and issued as U.S. Pat. No. 10,272,091, which claims the benefit of U.S. Provisional Application Ser. No. 61/903,362, filed Nov. 12, 2013. Each of the applications identified above is hereby incorporated by reference in its entirety.

FIELD OF THE INVENTION

The present invention relates to systems and methods for utilizing theacrine alone and in combination for use in providing physiological benefits. More particularly, the invention relates to theacrine and other naturally occurring compounds, whether produced synthetically or harvested from natural sources, and use of these chemical compounds to provide physiological benefits, which may vary according to theacrine concentration and the presence of synergists and antagonists.

BACKGROUND OF THE INVENTION

Tea is one of the most widely consumed products in the world. Tea and the different varieties of tea have been extensively studied. Many epidemiologic and preclinical studies suggest that drinking tea may reduce the risk of cancer and cardiovascular disease. Theacrine, an alkaloid purine similar to caffeine, is relatively rare and only found in a few varieties of tea (*kucha* tea, genus *Camellia*), the fruit cupuacu, and other plants related to coffee and cacao (genera *Coffea* and *Theobroma*), such as *Coffea liberica, Coffea dewevrei, Coffea abeokutae* and *Theobroma grandiflorum*.

1,3,7,9 tetramethyluric acid, commonly known as theacrine, was not studied until around 1975. However, it has been known of since about 1937, when it was detected in dry, decaffeinated *Camellia sinensis* tea leaves. At this time, the *Camellia assamica* var. *kucha* variety of tea is the primary source of naturally occurring theacrine and produces the chemical in higher concentrations than other known plants. Interestingly, theacrine has not been detected at all in more traditional teas strains. It is believed to be formed by methylation of caffeine and may be an intermediary in the production of liberine or other purines. Its natural function, if any, remains unknown. Theacrine has garnered attention only relatively recently, and often only as a secondary consideration when analyzing other compounds. Some studies suggest it may have beneficial qualities, such as serving as an effective anti-oxidant, anti-inflammatory and may have anti-obesity properties.

In the studies involving theacrine, beneficial effects may be at least partially attributable to an assortment of purine alkaloids and phenolic compounds. The more common tea-related purine alkaloids include caffeine, theobromine, theophyline and theacrine. The major tea phenolic compounds are gallic acid and eight naturally occurring tea catechins, including (+)-catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG).

Many different biologic and physiologic activities have been attributed to tea and its various components. However, only a few of its components have been studied in depth. Caffeine is by far the most studied, and the most commonly used stimulant found in tea. Theacrine appears to have an opposite effect, despite being very similar in chemical structure. Recent experiments have shown that theacrine exhibits a variety of activities, some of which seem inconsistent.

In the past several years, there has been a substantial shift in public opinion toward using naturally occurring chemical compounds for a variety of purposes, instead of synthetic chemicals. For example, a wide variety of natural chemicals are now commonly used as sedatives, e.g. valerian root and chamomile, anti-depressants, e.g. St. John's wort, stimulants, e.g. caffeine, and concentration, e.g. ginseng. In general, naturally occurring compounds may be easier for the body to digest and interact with and may include minimal and less severe side effects.

It is therefore desirable to identify naturally occurring chemical compounds and mixtures thereof that may provide benefits. It is also desirable to provide chemical compounds and mixtures thereof that may be used to provide a variety of benefits, varying by concentration, thus requiring production or harvesting of fewer materials.

SUMMARY OF THE INVENTION

Accordingly, the primary object of the present invention is to provide a chemical composition comprising theacrine, either naturally or synthetically produced, and optionally other chemicals, including theacrine congeners or analogs, to provide a plurality of desirable effects. Theacrine analogs may include, but are not limited to, caffeine, methyl caffeine, theobromine, theophylline, liberine and methylliberine, and their variants. Other suitable actives may include one or more ergogenic or nootropic compounds such as CDP choline, alpha-GPC, choline bitartrate, St John's Wort, sulbutiamine, and the like.

Theacrine exhibits a wide variety of effects depending on dosage. The presence of other ingredients may also modulate its effects. It may be used to promote calm or focus and to relax, but also may be used to enhance energy and stamina. It may also serve as an antioxidant and an anti-inflammatory.

In one embodiment, theacrine may be used to modulate stimulants, to provide heightened energy without heightened anxiety or nervousness. There may be variability among individuals, as described herein.

In another embodiment theacrine may be used as a mild sedative or relaxant.

In a further embodiment, theacrine may be used to promote weight loss, act as an antioxidant and as an anti-inflammatory. Theacrine may be used transdermally to enhance one or more of these effects.

In one embodiment, a dietary supplement comprising about 5 mg to about 850 mg theacrine, either natural or synthetic, is provided.

In another embodiment, a method of treatment for improving physical performance or energy in an individual is provided. Said method involves providing the individual with a composition comprising about 5 mg to about 850 mg of theacrine, either natural or synthetic, wherein upon administration of the composition the individual experiences improvement of at least one of mood, energy, focus, concentration or sexual desire or a reduction of at least one of anxiety or fatigue. In another embodiment, a second compound such as caffeine may also be administered in the composition.

It is therefore an object of the present invention to provide compositions including theacrine capable of imparting a plurality of positive effects.

It is another object of the present invention to provide congeners, derivatives and iterations of theacrine and synthetic chemical equivalents of theacrine.

It is another object of the present invention to provide agglomerated theacrine, theacrine salts, microencapsulated, liposomal or esterified theacrine.

It is another object of the present invention to provide theacrine combined with glycerides, propylene glycol, polyethylene glycol (PEG), lauroyl macrogol, lauroyl macrogol derivatives and co-crystallization products of theacrine.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

In one embodiment, theacrine may be co-administered with caffeine to produce a synergistic composition, wherein the co-administered caffeine reduces theacrine oral clearance and oral volume of distribution. The co-administered caffeine in the synergistic composition increases the bioavailability and maximum plasma concentration of theacrine in comparison with the corresponding pharmacokinetic parameters when theacrine is administered alone.

In one embodiment, a synergistic composition may comprise theacrine and caffeine having a weight to weight ratio about 1:1.2. Said synergistic composition may comprise about 125 mg theacrine and about 150 mg caffeine. Said synergistic composition may be administered once daily.

In one embodiment, a method of enhancing the intensity and duration of theacrine's neurocognitive efficacy beyond a systemic concentration threshold. Said method involves providing an individual with a synergistic composition comprising co-administration of theacrine and caffeine.

In one embodiment, a method of treatment for improving physical or mental performance in an individual is provided. Said method involves providing the individual with a synergistic composition comprising about 5 mg to about 850 mg of theacrine and about 25 mg to about 650 mg of caffeine. Upon administration of the synergistic composition, the individual experiences improvement of at least one of mood, energy, focus, concentration, cognitive function, or sexual desire or a reduction of at least one of anxiety or fatigue.

DETAILED DESCRIPTION OF THE INVENTION

Figure 1:
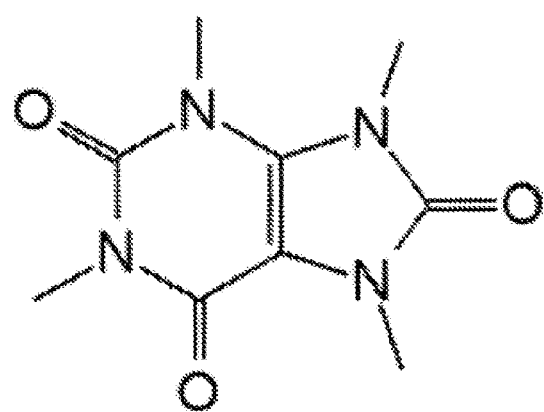
FIG. 1 depicts, in one embodiment, a molecular diagram of theacrine in accordance with the principles of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Disclosed is an invention relating to uses of theacrine, also known as 1,3,7,9-tetramethyluric acid, Temurin, Temorine, Tetramethyluric acid, Tetramethyl uric acid and 1,3,7,9-tetramethylpurine-2,6,8-trione. Theacrine may be produced synthetically or may be isolated from a natural source. Theacrine isolated from a natural source may be purified to 95% or greater. Optionally, less purification may be used such that theacrine accounts for 50%, or even less, of the material. In some embodiments, it may be preferable to utilize theacrine isolated from a natural source which may include other congeners of theacrine typically found in theacrine isolates.

In one embodiment, theacrine may be combined with other chemical compounds to provide a plurality of positive effects on a human or other animal. By altering the dosage of theacrine and/or chemical compounds it is combined with, various physiological effects may be selected for. The compositions may provide primarily a single benefit, or may provide multiple benefits simultaneously.

In another embodiment, theacrine may be used at lower dosage levels and/or in conjunction with compounds that modulate or antagonize its activity. Such compositions may induce an improved mood, higher energy, a reduction in fatigue, increased focus, increased concentration, increased mobility, decreased appetite, and increased stamina.

An advantage of using the invention may be the reduced likelihood that a person develops a tolerance to chemical compositions in accordance with the principles of the invention. That is, a person may not become desensitized to the effects induced.

In another embodiment, theacrine may be used at higher dosage levels and/or with synergistic compounds. These compositions may increase a person's basal/resting metabolic rate, increase thermogenesis, decrease appetite, enhance cognitive performance, increase Alpha wave brain activity, and/or induce euphoria. Without being bound by theory, the inventors believe that at higher dosage levels, theacrine may be noradrenergic and dopaminergic, and may exhibit increased adenosine receptor inhibition.

In another embodiment of the invention, theacrine may be combined with ephedrine, caffeine, salicylic acid or the like. These may be used to either modulate the more sedative effects of theacrine or optionally to interact synergistically with the more stimulating effects of theacrine. For example, theacrine may be combined with caffeine in order to modulate the excessive stimulatory effects of caffeine, thereby stabilizing heart rate and other metabolic activity. That is, a combination of theacrine and caffeine may result in a composition that imparts the increased focus and energy induced by caffeine, but without the higher heart rate and blood pressure due to modulation of caffeine by theacrine. Thus the combination may result in heightened awareness and calmness without the jitters caffeine may cause.

Theacrine and caffeine administered in combination has unexpected effects. Indeed, it has been unexpectedly found that a combination of theacrine and caffeine administered to human subjects results in increased levels of focus, concentration and energy as measured by 100 mm VAS scales while also decreasing measures of anxiety, irritability or feelings of overstimulation. Such decrease in anxiety, irritability, jitters and/or feelings of overstimulation is reflected by patients on standardized 100 mm VAS at durations of 30 minutes, 60 minutes, 120 minutes and 180 minutes as compared with administration of caffeine alone. The combination also exhibits a prolonged duration of action in increased energy, focus and/or concentration as compared to either caffeine or theacrine alone.

Furthermore, theacrine also has unexpected effects on the development of tolerance and habituation of caffeine. In a fourteen day study of repetitive dosing of theacrine and caffeine, it was found that the subjects maintained heightened psychometric indices of energy, focus, concentration, motivation to exercise, motivation to accomplish and finished tasks, and improved mood at Day 14 as compared to caffeine alone, and absolute levels of energy and motivation were greater than with theacrine alone. Those taking theacrine alone still maintained elevated subjective energy, focus, concentration, motivation to exercise, motivation to accomplish and finish tasks, sexual desire and improved mood with decreased anxiety as compared to Day 1. Subjects taking caffeine alone saw decreasing levels of energy, focus and concentration by Day 5 of the study and had increased anxiety scores throughout the study.

In another embodiment of the invention, theacrine may be combined with one or more bioavailability enhancers, including for example bioperine, piperine, black pepper, bergamottin, dihydroxybergamottin (CYP3A4 inhibitors), flavonoids (including hesperidin, naringin, tangeritin, quercetin and nobiletin both in isolation and in combination), pterostilbenes, fisetin, nanoencapsulation, microencapsulation, liposomes and/or phytosomes. Which enhancers are combined with theacrine may depend on which qualities of theacrine are desired for a particular use.

In another embodiment of the invention, theacrine may be introduced using one or more delivery methods, including, for example transdermal patches and/or creams, ready to mix powders, intravenous methods, capsules, tablets, liquid (including liquids for mixing with other beverages), softgels, shot format, and/or cosmetic applications including soaps, lotions and shampoos. Theacrine's anti-inflammatory qualities may be desired for a variety of topical applications.

In another embodiment of the invention, theacrine may be used to provide sports performance enhancers that may reduce fatigue, improve mobility, and improve alertness.

In another embodiment of the invention, theacrine may be used as a topical agent for incorporation into body creams or lotions to produce a cream or lotion for lightening skin, firming skin, and/or improving skin elasticity. A theacrine topical agent may also be used to promote localized transdermal fat loss. Theacrine may also be used in a cream or lotion to promote localized enhanced metabolism and/or enhanced thermogenesis.

In another embodiment of the invention, theacrine may be combined with one or more of an analgesic, for example ibuprofen or salicylic acid, anti-inflammatory agents, salicin, fish oil (omega-3 fatty acids and specialized, small lipid pro-resolving derivatives), tart cherry, krill oil, astaxanthin, proteolytic enzymes, glucosamine sulfate, chondroitin sulfate, MSM (methyl sulfonylmethane), SAMe (S-adenosylmethionine), ASU (avocado-soybean unsaponifiable fraction), cetyl myristoleate, Dolichos falcate and/or triterpenoids.

Theacrine itself can reduce biomarkers of inflammation in humans in response to acute inflammatory stressors (e.g., intense exercise) or chronic consumption. Theacrine is shown to decrease C-reactive protein (CRP), Erythrocyte sedimentation rate (ESR), interleukin-6 (IL-6) and TNF-alpha.

In another embodiment of the invention, theacrine may be combined with extracts from one or more of *Acacia catechu, Andrographis paniculata, Scutalleria baicalensis*, agmatine sulfate, Stinging Nettle, Sea Buckthorn, curcumin, *Cissus Quadrilangularis, Boswellia Serrata, Wasabia japonica* (wasabi extract for Tea Tree Oil), Emu Oil, Arnica, *Mangifera indica* L. (Anacardiaceae), *Lagenaria breviflora*, and/or *Zingiber officinale* (ginger & gingerols/shogaols). Such a combination may be used in, for example, methods of augmenting and enhancing pain modulation, and controlling the inflammatory response.

In another embodiment of the invention, theacrine may be combined with one or more metabolic enhancers including hoodia gordonii, caffeine, yohimbine, synephrine, theobromine, flavonoids, flavanone glycosides such as naringin and hesperidin, tocopherols, theophylline, alpha-yohimbine, conjugated linoleic acid (CLA), octopamine, evodiamine, passion flower, red pepper, cayenne, raspberry ketone, guggul, green tea, guarana, kola nut, any beta-phenethylamines, *Acacia rigidula*, and/or forskolin (*Coleus forskohlli*). Such a combination may be used in, for example, methods of enhancing 1) thermogenesis/fat and carbohydrate metabolism; 2) fat loss, weight management and improving body composition (loss of body fat, while retaining or sparing lean body mass/fat free mass/muscle); and/or 3) appetite control/appetite modulation.

Combinations of theacrine and, for example, caffeine, theobromine, or flavanone glycosides such as naringin or hesperidin, upon administration to subjects show decreased VAS 100 mm ratings of perceived physical exertion with exercise as compared to ingredients alone. Theobromine is used by some for improvement of breathing or a subjective feeling of improved breathing, but is also known to increase feelings of anxiety, jitters and an elevated heart rate in some subjects. A combination of theobromine and theacrine retains the beneficial effects while reducing the unwanted anxiety, jitters and/or elevated heart rate effects.

In another embodiment of the invention, theacrine may be combined with anti-fatigue, focusing and/or energy enhancing ingredients including caffeine, theobromine, theophylline, synephrine, yohimbine, rhodiola, ashwagandha, ginseng, *Ginkgo Biloba*, siberian ginseng, astragalus, licorice, green tea, reishi, dehydroepiandrosterone (DHEA), pregnenolone, tyrosine, N-acetyl-tyrosine, glucuronolactone, taurine, choline, CDP-choline, alpha-GPC, acetyl-L-carnitine, 5-hydroxytryptophan, tryptophan, any beta-phenethylamines, *Sceletium tortuosum* (and Mesembrine alkaloids), *Dendrobium* sp., *Acacia rigidula*, PQQ (*Pyroloquinoline quinone*), Ubiquinone(ol), Nicotinamide riboside, picamilon, Huperzine A (Chinese clubmoss) or *Huperzia serrata*, L-dopa, *Mucuna pruriens*, forskolin (*Coleus forskohlli*). Such a combination may be used in, for example, methods for enhancing cognitive function, including focus, concentration, sustained attention, working memory, choice and non-choice reaction time, executive function, verbal and non-verbal learning, visuospatial memory and verbal fluency.

In a further embodiment, theacrine may be combined with a nutritional cholinergic ingredient such as 2-(dimethylamino)ethanol (DMAE), DMAE bitartrate, choline bitartrate, alpha-GPC (alpha-glycerophosphorylcholine), Huperzine A, CDP choline, or combinations thereof. One of skill in the art will recognize that these are merely examples of cholinergic ingredients and that other such cholinergic ingredients not listed are also contemplated by the present invention. The combination of a nutritional cholinergic ingredient with theacrine can result in a synergistic effect of increased psychometric measures for attention, focus and concentration beyond either the theacrine alone or cholinergic ingredient alone.

In another embodiment, any of the above combinations may be used with an isomer of, congener of, derivative of and/or a metabolite of theacrine such as, for example, liberine or methylliberine. Other suitable examples include methylated theacrine, nitrate salts of theacrine, oxidized theacrine, reduced theacrine and/or theacrine salts. Agglomerated theacrine, microencapsulated theacrine, liposomal theacrine, esterified theacrine, theacrine glycerides, and mixtures of theacrine with propylene glycol, lauroyl Macrogol, polyethylene glycol, theacrine derivatives, and/or theacrine co-crystallization products may also be used in accordance with the principles of the invention. Such use of these, as well as co-crystals or other conjugates (such as quercetin or pterostilbenoids), theacrine salts including citrate, salicylate, malate, tartrate, fumarate, succinate, nitrate, sulfate, phosphate and the like, or PEG-ylated (Macrogol) preparations may increase the functional efficacy of the theacrine.

In another embodiment, congeners of theacrine, for example catechins and other flavonoids, may be used an isolated, either independently or in combination with theacrine-based compositions.

The dosage of theacrine may range from about 5 mg to about 850 mg. In another embodiment, the range may be from about 65 mg to about 300 mg. In relation to the weight of the human subject, in one embodiment the dosage may be expressed as about 0.75 mg/kg of body weight to about 3 mg/kg of body weight. In initial trials the human ED90 appears to be about 1 mg/kg to about 3 mg/kg.

In one aspect of the invention, the theacrine may be administered with caffeine. When administered with caffeine, the ratio of caffeine to theacrine, weight to weight, may range from about 0.5:1 to about 50:1, and in another embodiment, from about 1:1 to about 10:1, and in a further embodiment, from about 2:1 to about 4:1. In administration, the theacrine may be administered in an amount of about 5 mg to about 800 mg with caffeine amounts ranging from about 25 mg to about 650 mg. In another embodiment the theacrine may be administered in an amount of about 5 mg to about 650 mg with the caffeine, and in other embodiments may be any amount in that range. Such administration provides an increase, as measured by 100 mm VAS scales, in at least one of focus, concentration and energy, while also providing a decrease in at least one of anxiety, irritability, and feelings of overstimulation. Recommended dosages expressed in terms of amount per body weight can range from about 0.75 mg/kg to about 3 mg/kg of theacrine when administered in combination with caffeine, although theacrine may be administered in the ranges described above up to about 850 mg regardless of whether it is administered in combination with caffeine.

The invention may be used for the treatment of a variety of conditions, such as improvement of mood, energy, focus, or concentration. The invention may also promote a reduced appetite, reduce the perceived exertion from exercise, decrease the discomfort associated with intense exercise, and may also improve sexual desire.

EXAMPLES

Example 1

In order to examine the beneficial experiential effects and psychometric properties of theacrine supplementation in healthy subjects, explore optimal dosing and potential cumulative effects in a healthy human cohort with a 7-day, sub-acute repetitive dosing protocol, and acquire preliminary data on various biomarkers of safety and tolerability, an experiment was performed.

15 healthy subjects (mean±SD age, height, wgt, BMI: 28.3±6.1 y, 175.7±11.5 cm, 89.8±21.7 kg, 29.1±4.7) ingested 200 mg of TeaCrine™ (Compound Solutions, Inc., Carlsbad, Calif.) (TC) or Placebo (PLA). Anchored VAS questionnaires were used to detect changes in various aspects of physical and mental energy and performance; side effect profiles, hemodynamics and biochemical markers of safety were also collected over a 3-hr post-dosing period. A subset of 6 subjects underwent a separate 7-day, open-label, repeated dose study comparing 100 mg, 200 mg and 400 mg of TC.

The experiment was a randomized, placebo-controlled, double-blind, within-subject crossover clinical trial (for N=15 study). A further subset study was open-label, sub-acute (7-day), repetitive dosing trial (for N=6 subset).

Six (6) subjects provided written and dated informed consent to participate in the 7-day repetitive dosing study between Dec. 15, 2012 and Feb. 21, 2013. A separate cohort of fifteen (15) subjects provided written and dated informed consent for the acute dose, placebo-controlled, crossover clinical trial. All subjects were in good health as determined by physical examination and medical history, between the ages of 18 and 45 (inclusive). Subjects' caffeine intake from foods/beverages was limited to <300 mg daily. Subjects were willing and able to comply with the experimental and supplement protocol.

Excluded subjects included subjects who were pregnant or lactating, subjects with a history of hepatorenal, musculoskeletal, autoimmune, or neurologic disease, diabetes, thyroid disease, adrenal disease, hypogonadism, inborn error of metabolism, personal history of heart disease, high blood pressure (systolic>140 mm Hg & diastolic>90 mm Hg), psychiatric disorders, cancer, benign prostate hypertrophy, caffeine sensitivity, gastric ulcer, reflux disease, or any other medical condition deemed exclusionary by the medical staff, subjects currently taking thyroid, hyperlipidemic, hypoglycemic, anti-hypertensive, anti-coagulant medications or OTC products containing pseudoephedrine or other stimulants, subjects who had used any weight-loss supplements within 30-days prior to the study, subjects who had gained or lost more than 10 lbs within the past 30 days, subjects who drank more than one cup of percolated coffee or 2 cups of tea per day, subjects who smoked or had quit smoking within the past six months, subjects who had a known allergy to any of the ingredients in the supplement or the placebo, and subjects who did not demonstrate a verbal understanding of the Informed Consent document.

The study did not incorporate a dietary intervention (other than supplement/placebo ingestion). Subjects were instructed to complete a 24-hr diet record prior to their first laboratory visit, and duplicate that 24-hr diet prior to each subsequent laboratory visit. The study also did not incorporate any physical activity intervention. Subjects refrained from exercise and/or heavy physical activity the day prior to each laboratory visit.

Physical activity levels and health history were determined using standardized questionnaires. Heart rate and blood pressure were measured using an Omron HEM-780. Standing height was determined using a wall-mounted stadiometer. Body weight was measured using a Seca 767™ Medical Scale. A 100 mm anchored VAS questionnaire for energy, fatigue, and concentration was distributed at each acute lab session; additional VAS questionnaires were distributed for the daily assessment over a 6-hour period during the 7-day subset study. Quest Diagnostics (Pittsburgh, Pa.) was utilized to transport and analyze all blood samples. For each laboratory session, subjects reported to the lab well hydrated, 10-12 hours postprandial, and at least 24-hours after their last exercise session.

Statistical Analyses:

Descriptive statistics (mean, median, SD, 95% CIs) were used to quantify subjects physical characteristics. RM ANOVA, as well analyses of co-variance (ANCOVA), using baseline scores as the co-variate (respectively), were used to analyze between trial differences. Alpha was set to 0.05 (P≤0.05) for statistical significance, and <0.10 for trends. Effect sizes were also calculated. Upon arrival for the first testing session, subjects were randomly assigned to receive their respective supplement/placebo. Each subject ingested the sponsor recommended dosage of their respective supplement (1 capsule prior to schedule of assessments). Supplements were prepared in capsule form and packaged in coded generic containers for double-blind administration.

Results:

The 200 mg dose of TC caused significant improvements in energy (TC: +8.6% vs. PLA: −5.7%, P=0.049) and reductions in fatigue (TC: −6.7% vs. PLA: +5.8%, P=0.04). A trend for improved concentration was also noted (TC: +2.4% vs. PLA: −1.3%, P=0.07). No changes in systemic hemodynamics or side effect profiles were noted. The N=6 cohort study demonstrated moderate to large effect sizes (0.50 to 0.71) with the 200 mg dose of TC over a 7-day period of assessment for the following subjective measures: energy, fatigue, concentration, anxiety, motivation to exercise and libido.

The results of the experiment are also shown graphically in FIGS. 2 through 7.

Figure 2:
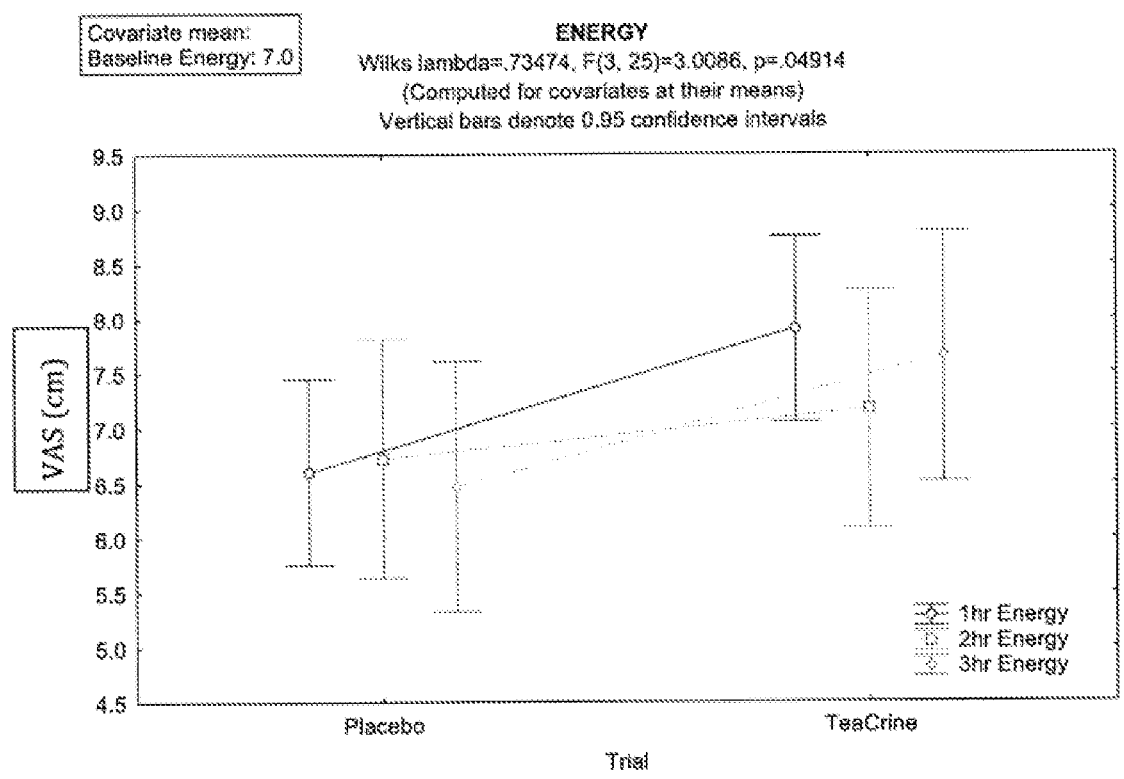
FIG. 2 depicts, in one embodiment, a graph of results of a trial showing perceived energy on a VAS scale (0 to 10 cm) at 1, 2 and 3 hours after administration of theacrine or placebo.
Figure 3:
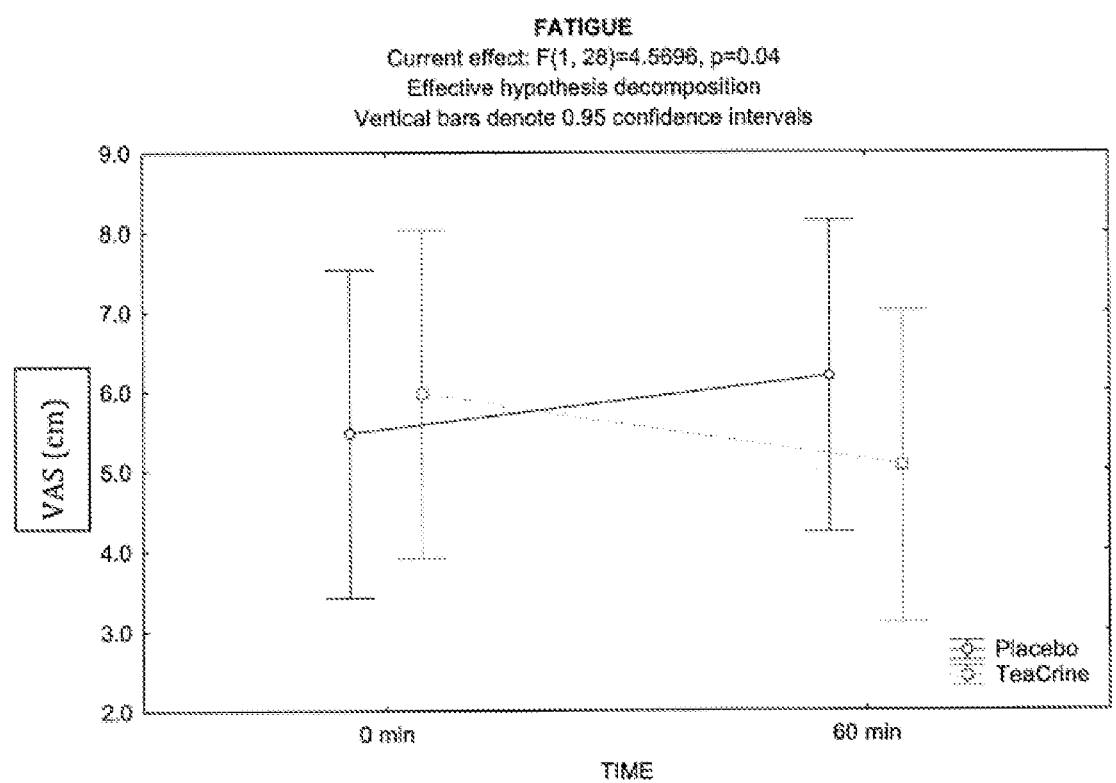
FIG. 3 depicts, in one embodiment, a graph of results of a trial showing perceived fatigue on a VAS scale (0 to 10 cm) at 0 minutes and 60 minutes after administration of theacrine or placebo.
Figure 4:
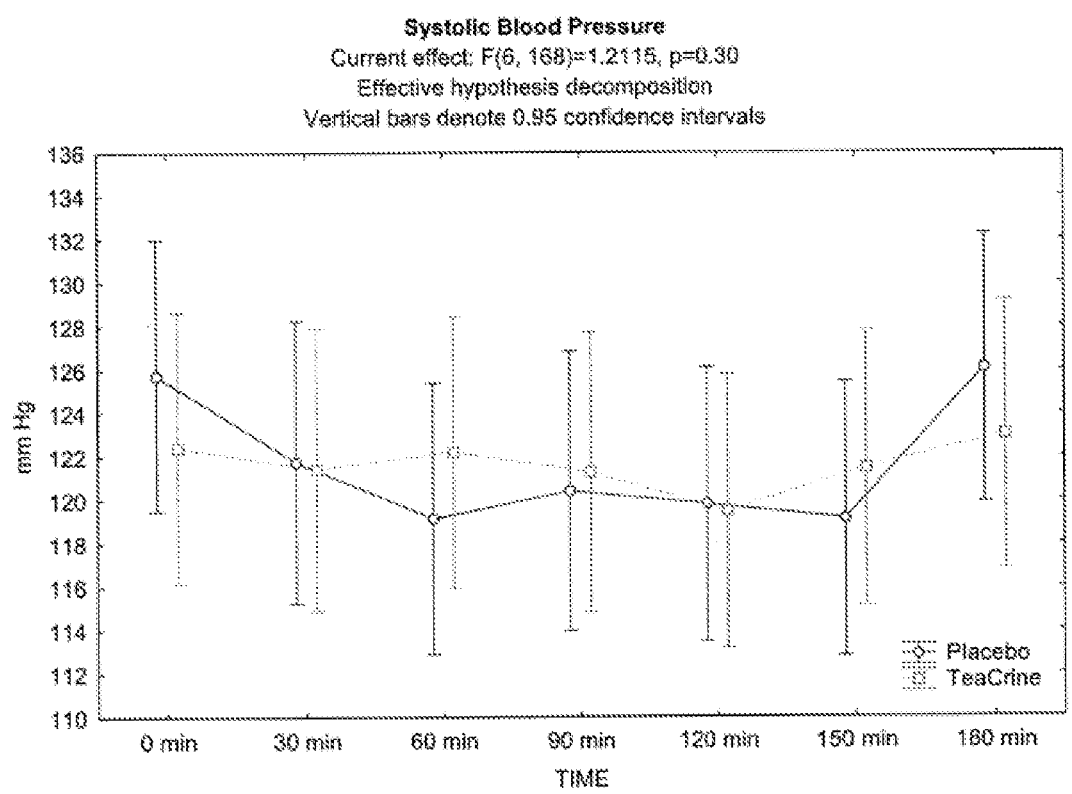
FIG. 4 depicts, in one embodiment, a graph of results of a trial showing systolic blood pressure at various time intervals after administration of theacrine or placebo.
Figure 5:
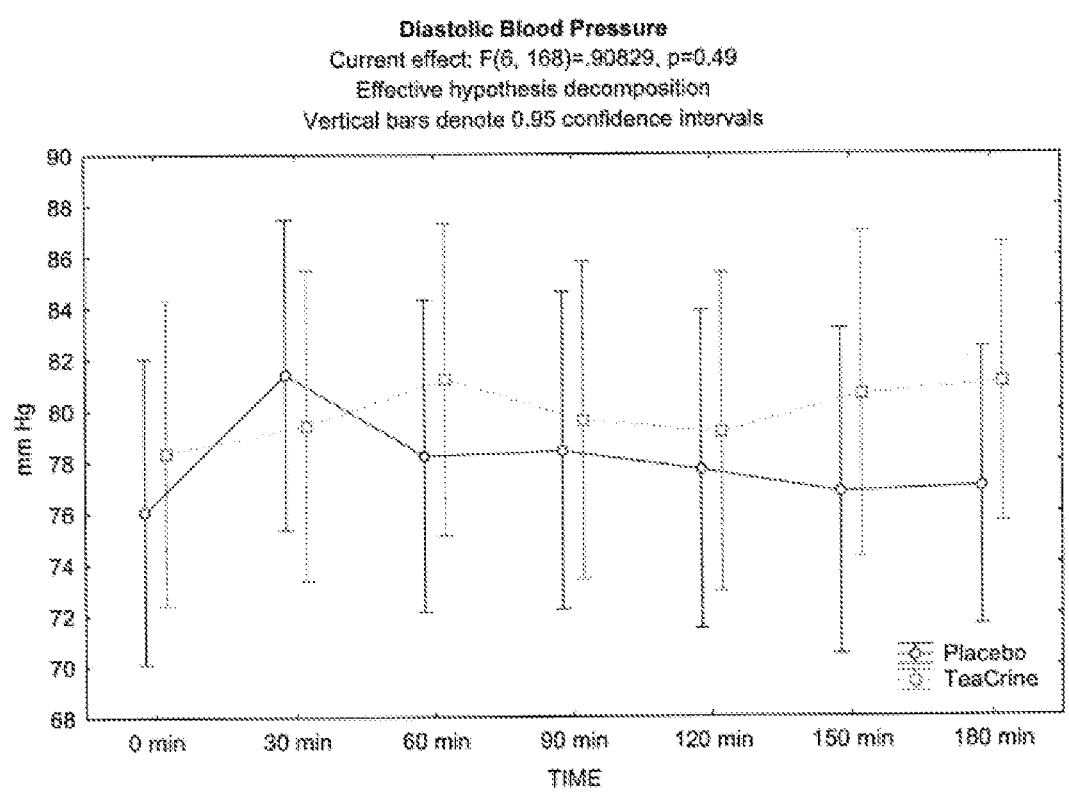
FIG. 5 depicts, in one embodiment, a graph of results of a trial showing diastolic blood pressure at various time intervals after administration of theacrine or placebo.

As shown in FIG. 2, individuals who were administered theacrine reported higher levels of energy at each time increment measured. FIG. 3 shows that while individuals given the placebo reported higher fatigue at 60 minutes after administration, those administered theacrine reported lower levels of fatigue. FIGS. 4 and 5 show that no substantial change in systemic hemodynamics occurred.

Figure 6:
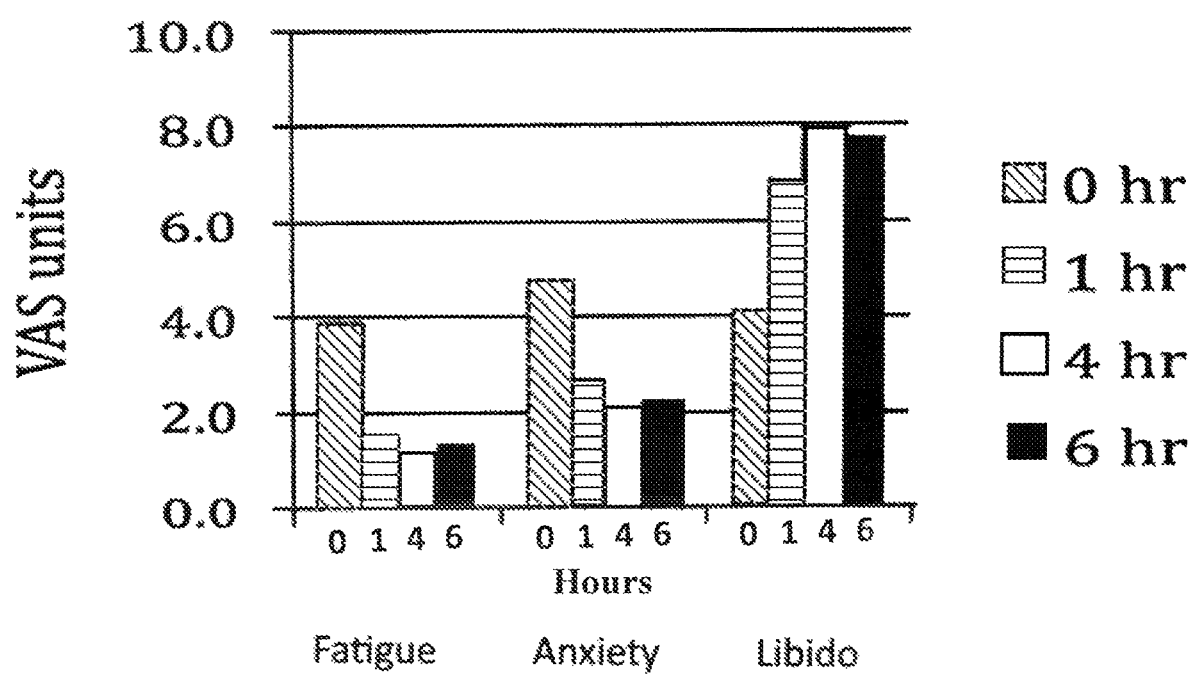
FIG. 6 shows, in one embodiment, the results of a 7 day repeated dose study of 200 mg theacrine relative to baseline of fatigue, anxiety and libido at various intervals after dosages (at 0 hr, 1 hr, 4 hr, 6 hr; bars left to right for each measured category). Effect size of 200 mg dose of TC over course of 7-day repeated dose study relative to baseline on: Fatigue: 0.64, Anxiety: −0.59, Libido: 0.71. Units for vertical axis are Visual Analogue Scale (in cm).
Figure 7:
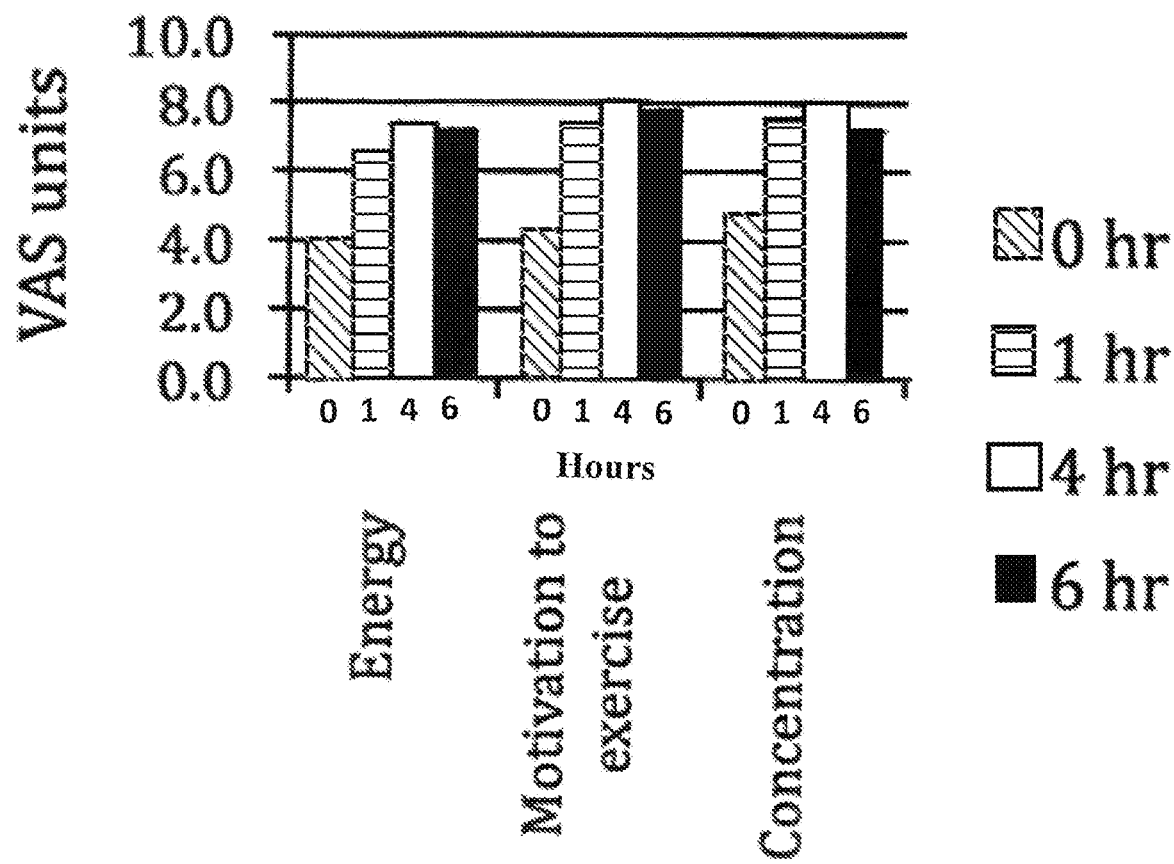
FIG. 7 shows, in one embodiment, the results of a 7 day repeated dose study of 200 mg theacrine relative to baseline of energy, motivation to exercise, and concentration at various intervals after dosages (at 0 hr, 1 hr, 4 hr, 6 hr; bars left to right for each measured category). Effect size of 200 mg dose of TC over course of 7-day repeated dose study relative to baseline on: Energy: 0.63, Motivation to Exercise: 0.58, Concentration: 0.60. Units for vertical axis are Visual Analogue Scale (in cm).

FIGS. 6 and 7 show the results of the N=6 cohort study. With a 200 mg dose of theacrine over a 7 day period of assessment, it was observed that theacrine has a positive effect on each of energy, fatigue, concentration, anxiety, motivation to exercise, and libido. That is, fatigue and anxiety were decreased substantially, while energy, concentration, motivation to exercise and libido were increased substantially.

Thus, the experimental data shows that theacrine supplementation appears to favorably impact several subjective and psychometric indices of energy and fatigue. These findings, as well as the potential cumulative effects on focus, concentration, and libido are worthy of future study.

Although previously published animal data suggested much larger doses of "TC" would be necessary to exert its neurophysiological effects, this first-in-human data suggests much lower doses of 1.5 mg to 2.5 mg/kg bodyweight (for example, approximately 200 mg in a 100 kg individual) provide optimal benefit. Follow-up studies should confirm these results, explore other objective measures of physical and cognitive function, and clarify the mechanisms by which theacrine exerts the observed salutary effects.

Example 2

Assessment of the Drug-Drug Interaction Potential Between Theacrine and Caffeine in Humans Theacrine pharmacokinetics in humans has not been systematically characterized. Therefore, one purpose of this study, among others, was to determine theacrine pharmacokinetics and dose-linearity following oral administration in humans. Another purpose of this study is to determine whether or not caffeine alters theacrine pharmacokinetics and/or pharmacodynamics, when both ingredients are ingested together.

Eight healthy nonsmokers, including 4 men and 4 women, were recruited for the experiment. The test subjects regularly consumed stimulants (i.e., caffeine, 50-400 mg/day) with beverages or nutritional supplements. The same test subjects did not have a history of adverse reactions to caffeine or other stimulants.

Study Design and Procedures

This study was a randomized, double-blind, 4-arm crossover design with each subject receiving 4 treatments consisting of theacrine (25 mg), theacrine (125 mg), caffeine (150 mg), and theacrine (125 mg) plus caffeine (150 mg), respectively. Theacrine, administered as iTeaCrine®, was provided by Compound Solutions (Carlsbad, Calif.). Caffeine, administered as caffeine anhydrous, was obtained from Nutravative Ingredients (Allen, Tex.). Treatment sequence was randomized using a 4×4 Latin square. There was an approximate 1-week washout period between treatments for all subjects.

Test Visit Procedures

Each study day, subjects reported to the lab between 6:00 and 7:00 am after a 10-hour fast and abstinence from beverages, drugs, or supplements containing alcohol or caffeine (72-hours) and strenuous physical exercise (24-hours). A catheter was inserted into the forearm vein for blood sampling. Duplicate measurements of resting heart rate and blood pressure were taken pre-dose and prior to each timed blood sample. In addition, respiratory rate was counted in one minute and body temperature was measured using an ear scanning thermometer (dual readings taken at each time). At approximately 8:00 am, each subject received a single oral dose of a theacrine, caffeine, or combined theacrine-caffeine composition accompanied by water. Blood samples at 0 minute (5 samples obtained for baseline prior to administration of the oral compositions), 15 minutes, 30 minutes, 60 minutes, and 90 minutes, and 2, 4, 6, 8, and 24 hours post-administration. Collected samples were processed and stored in multiple aliquots (~500 µL, −70° C.) until analyzed for theacrine, caffeine, and paraxanthine using LC-MS/MS.

All subjects were instructed to consume their usual diet throughout the study period, with the exception of the actual days of testing. During the two days prior to each test day, subjects recorded all food and drink consumed and attempted to mimic this intake for the two-day period prior to subsequent visits. Diet records were analyzed using nutrient analysis software (Food Processor SQL, version 9.9; ESHA Research, Salem, Oreg.). For the actual test days, standardized meals (meal replacement food bars [Clif "Builder's 20 g Protein Bar"] and ready-to-drink shakes [Orgain Organic Nutrition™]) were provided to the subjects after sample collection at hour 2 and hour 6 (one shake and one-half bar at each time). Subjects were also provided with adequate meal replacement bars and shakes to consume following the 8 hour sample collection. (during their time outside the lab). Each bar contained 280 calories, 10 grams of fat, 29 grams of carbohydrate, and 20 grams of protein. Each shake contained 250 calories, 7 grams of fat, 32 grams of carbohydrate, and 16 grams of protein. No food other than what was provided to the subjects was allowed during each study day, including both time spent in the lab and outside the lab. The only beverage that the subjects were allowed to consume was water and the volume consumed while in the lab was matched for each test day (men: 94±25 ounces; women: 78±17 ounces). The subjects returned the following morning for the 24 hour blood collection, again in a 10 hour fasted state. The same volume of meal replacement bars or shakes was consumed by each subject during each visit (both in lab and outside lab). All the subjects except one female consumed 3 shakes and 3 bars during the period of time outside the lab. Said female subject only consumed 2 bars and 2 shakes. Physical activity remained similar for all the subjects throughout the study period, with the exception of refraining from strenuous physical activity during the 24-hour period prior to each test day and for the actual test day itself.

Pharmacokinetic Study

Plasma concentration-time data were evaluated using noncompartmental methods in Phoenix WinNonlin (version 7.0; Pharsight Corporation, Mountain View, Calif.) with adjustment for lag time after oral administration. The maximum concentration ($C_{max}$), lag time ($t_{lag}$), and time of maximum concentration ($t_{max}$) were determined from the plasma concentration versus time data. The area under the plasma concentration-time curve from time 0 to infinity (was calculated using the trapezoidal rule extrapolated to time infinity). The terminal half-life ($t_{1/2}$) was calculated using the following function: $t_{1/2}=0.693/k$, wherein k is the constant of terminal rate elimination estimated from the slope of the linear portion of the log plasma concentration versus time curve. The oral clearance (CL/F) was calculated by dividing the oral dose by $AUC_{0-\infty}$. The apparent volume of distribution during the terminal elimination phase (Vz/F) was calculated by dividing CL/F by k.

Statistical Analysis

Differences between treatment group values were determined for systolic blood pressure (SBP), diastolic blood pressure (DBP), rate pressure product, and heart rate. Parametric data were analyzed by paired Student's t tests of mean differences in values between treatment groups. Statistical significance was defined a priori as a 2-sided or <0.05. The probability of interaction magnitude between theacrine and caffeine was determined using 90% confidence intervals about the geometric mean ratio of the observed pharmacokinetic parameters.

Results

Subject characteristics.

Eight physically active and healthy men (n=4; age 34.5±7.0 years; weight 94.3±13.1 kg) and women (n=4; age 22.5±3.9 years; weight 66.4±10.1 kg) completed this study. Men ingested a daily amount of caffeine equal to 143.8±168.7 mg, while women ingested 144.3±139.7 mg. All the subjects tolerated the treatments well and no adverse events were noted. Dietary intake was not different across treatment conditions for calories, macronutrients, or micronutrients (p>0.05).

Pharmacokinetics

Figure 8A:
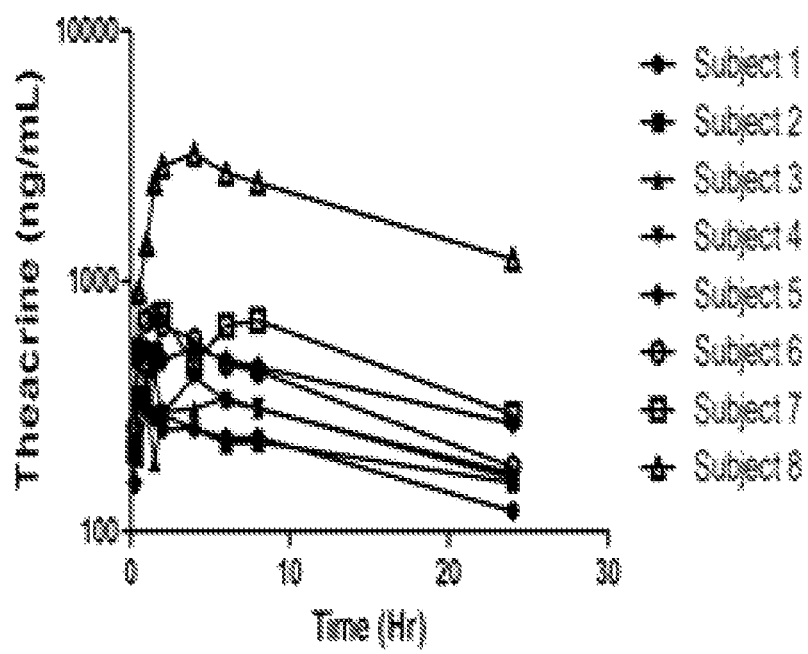
FIG. 8(A) depicts, in one embodiment, individual plasma concentrations of theacrine after single oral dose of theacrine 25 mg.
Figure 8B:
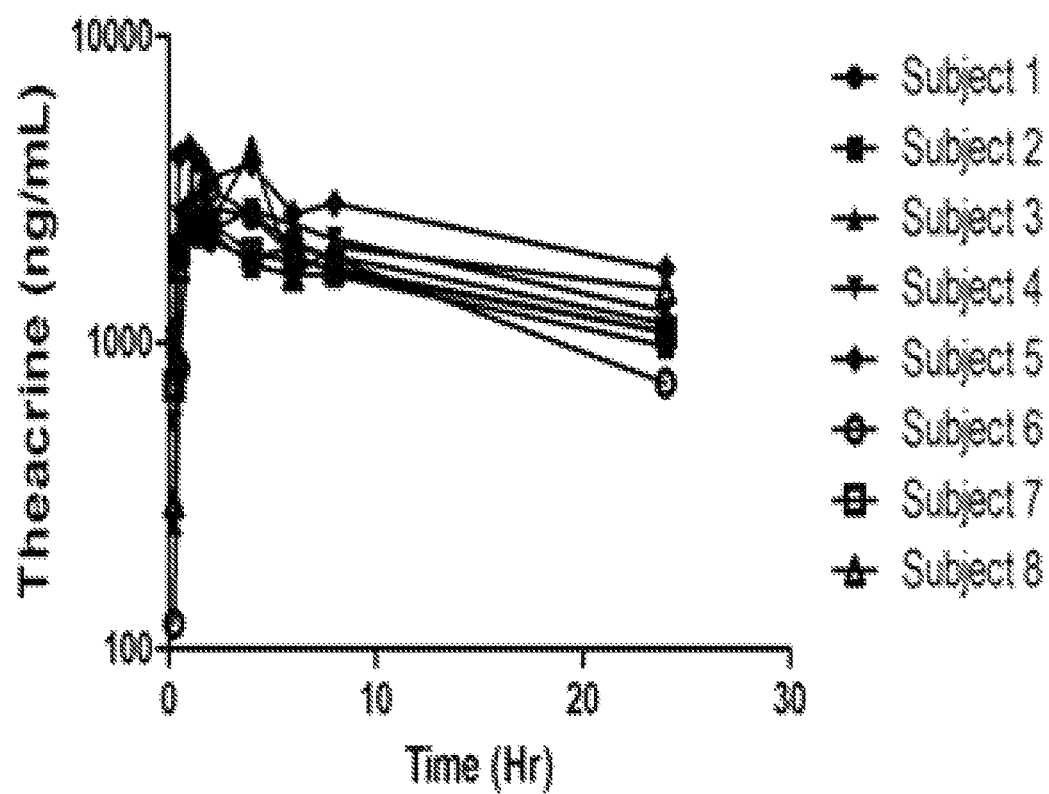
FIG. 8(B) depicts, in one embodiment, individual plasma concentrations of theacrine after single oral dose of theacrine 125 mg.
Figure 8C:
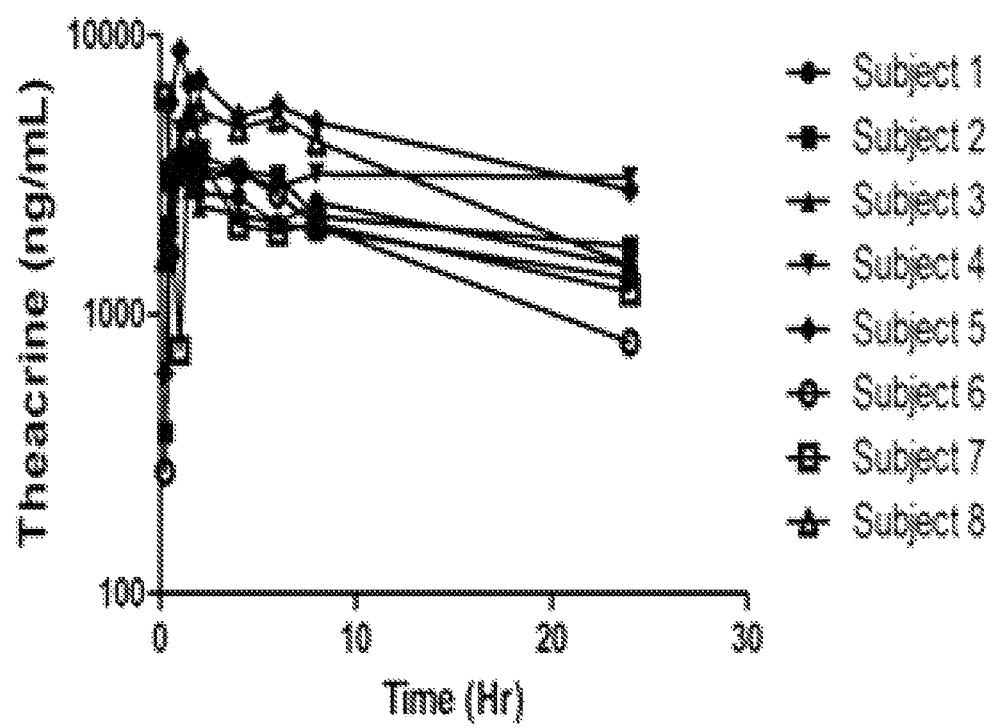
FIG. 8(C) depicts, in one embodiment, individual plasma concentrations of theacrine after single oral dose of theacrine 125 mg plus caffeine 150 mg.
Figure 9:
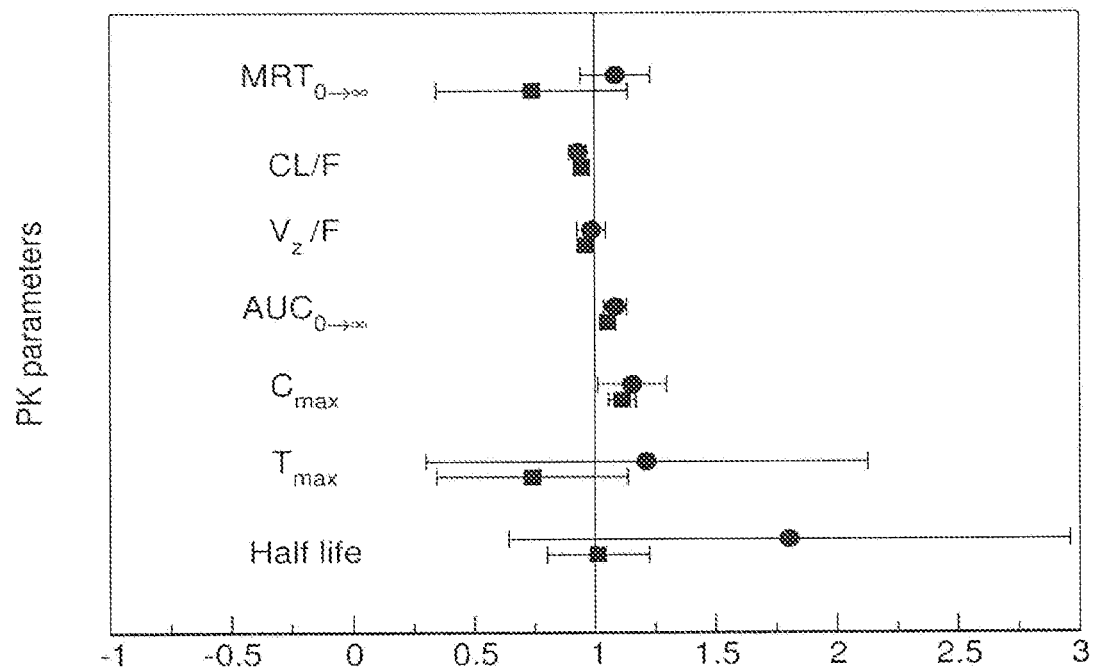
FIG. 9 depicts, in one embodiment, Forest plot illustrating the probability of interaction magnitude between theacrine and caffeine using 90% confidence intervals about the geometric mean ratio of the observed pharmacokinetic parameters following a single theacrine dose (.circle-solid.-25 mg theacrine and .square-solid.-125 mg theacrine in combination with 150 mg caffeine). $MRT_{0-\infty}$, mean residence time zero to infinity; CL/F, oral clearance; Vz/F, oral volume of distribution; $AUC_{0-\infty}$, area under the curve from zero to time infinity (dose normalized); $C_{max}$, maximum plasma concentration (dose normalized; $T_{max}$, time to reach maximum plasma concentration.
Figure 10A:
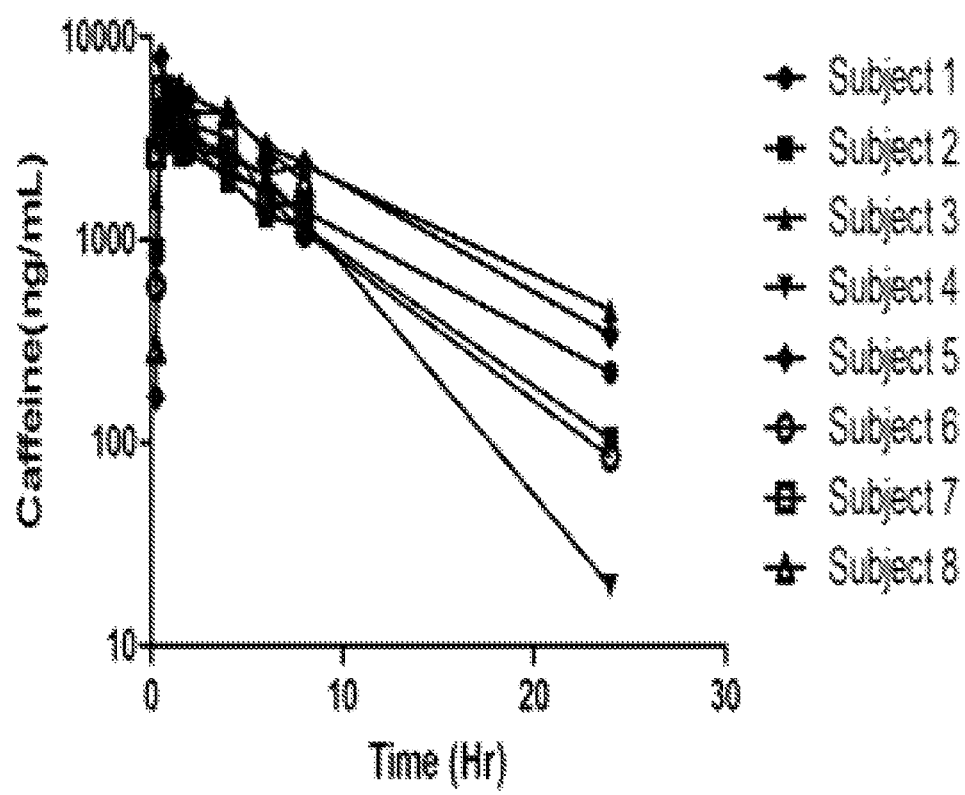
FIG. 10(A) depicts, in one embodiment, individual plasma concentrations of caffeine after single oral dose of caffeine 150 mg.
Figure 10B:
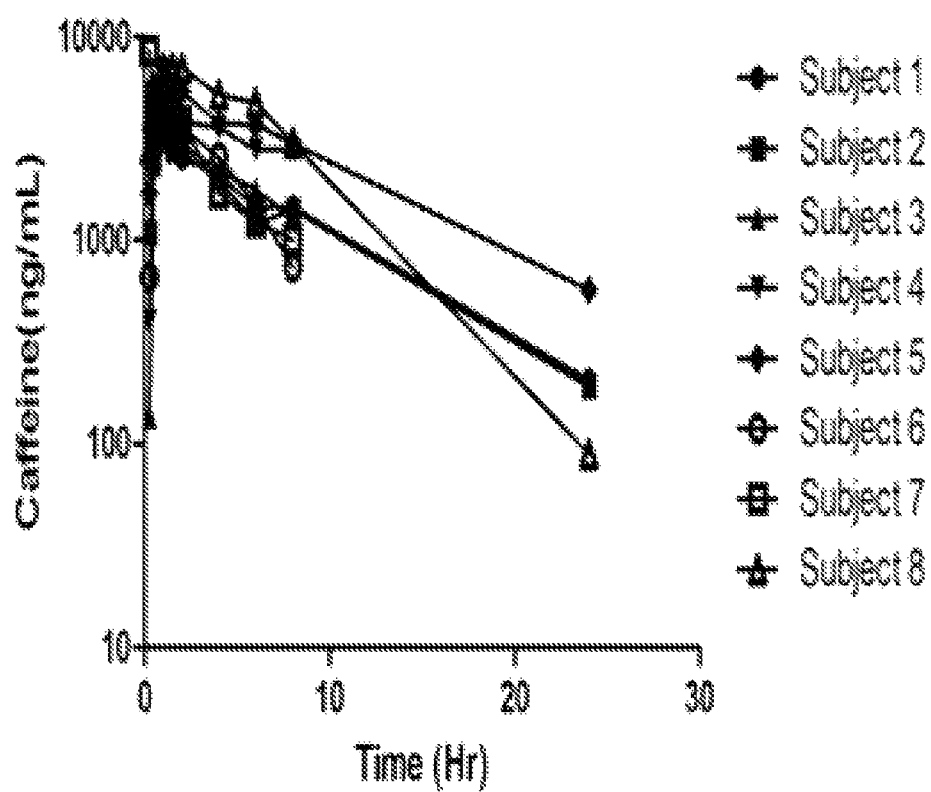
FIG. 10(B) depicts, in one embodiment, individual plasma concentrations of caffeine after single oral dose of theacrine 125 mg plus caffeine 150 mg.
Figure 11:
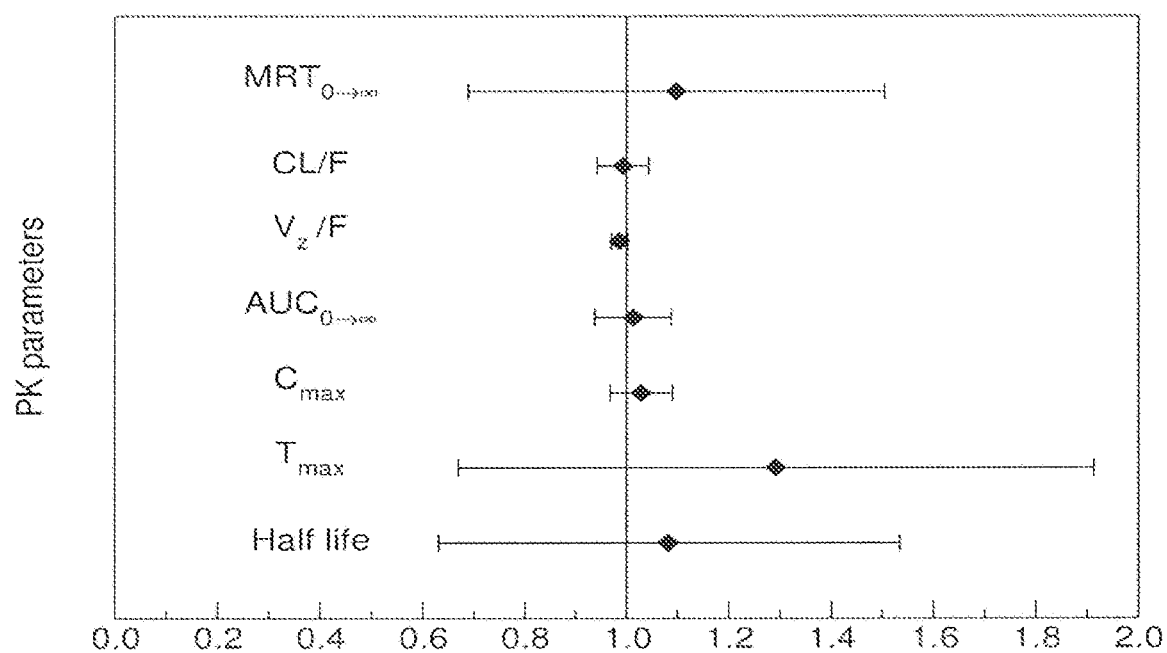
FIG. 11 depicts, in one embodiment, Forest plot illustrating the probability of interaction magnitude between caffeine and theacrine using 90% confidence intervals about the geometric mean ratio of the observed pharmacokinetic parameters following a single caffeine dose (150 mg) alone or in combination with theacrine (125 mg). Abbreviations: MRT0-∞, mean residence time zero to infinity; CL/F, oral clearance; Vz/F, oral volume of distribution; AUC0-∞, area under the curve from zero to time infinity (dose normalized); $C_{max}$, maximum plasma concentration (dose normalized); $T_{max}$, time to reach maximum plasma concentration.

Mean plasma concentration time profiles for theacrine, caffeine, and paraxanthine are shown in FIGS. 8, 9, and 10. Theacrine is well absorbed following oral administration of theacrine alone reaching maximal concentration within approximately 2 hours. Dose-adjusted theacrine pharmacokinetic parameters were not significantly different (Table 1). Theacrine absorption rate ($T_{max}$) and half-life ($t_{1/2}$) were unaffected by caffeine co-administration. However, caffeine co-administration significantly increased both mean theacrine exposure parameters $C_{max}$, (38.6±16.6 versus 25.6±5.5 ng/mL) and AUC (1.2±1.1 versus 0.74±0.31 hr*µg/mL/mg) as well as geometric mean ratios (1.1±0.06 and 1.1±0.03) (Table 2). Moreover, caffeine decreased both theacrine oral clearance (CL/F, 1.6±0.49 versus 1.2±0.56 L/hr) and oral volume of distribution (Vd/F, 50.5±0.49 versus 35.4±12.4 L) by approximately 30%. Of note, theacrine exposure (AUC) was consistently higher in Subject 8 than all other subjects in all treatment arms. However, caffeine pharmacokinetics in Subject 8 was similar to the other seven subjects. Caffeine pharmacokinetics is similar following caffeine alone or caffeine plus theacrine co-ingestion (FIGS. 10 and 11 and Table 2). Likewise, theacrine co-ingestion did not alter paraxanthine exposure parameters suggesting caffeine metabolism was unaffected by theacrine (Table 3).

TABLE 1

Theacrine Pharmacokinetics

| Parameter[a] | Condition 1[b] | Condition 2[c] | Condition 4[d] |
|---|---|---|---|
| $C_{max}$ (ng/mL) | 34.1 ± 38.9 | 25.6 ± 5.5 | 37.7 ± 16.5 |
| $T_{max}$ (hours) | 1.8 (0.5-6.0) | 1.8 (1.0-4.0) | 1.0 (0.3-2.0) |
| $t_{1/2}$ (hours) | 16.5 ± 2.4 | 26.1 ± 13.7 | 29.2 ± 25.3 |
| AUC (hr*ng/mL/mg) | 809 ± 923 | 736 ± 312 | 1,242 ± 1,129 |
| CL/F (L/hr) | 2.0 ± 0.9 | 1.6 ± 0.5 | 1.2 ± 0.6 |
| Vd/F (L) | 48.1 ± 23.4 | 51.0 ± 8.5 | 35.4 ± 12.4 |
| MRT (hours) | 24.9 ± 3.5 | 36.8 ± 18.9 | 41.7 ± 38.8 |

[a]$T_{max}$ values are expressed as median (range). All other values are expressed as mean ± SD and represent dose-adjusted pharmacokinetic parameters.
[b]Theacrine 25 mg
[c]Theacrine 125 mg
[d]Theacrine 125 mg + Caffeine 150 mg

TABLE 2

Caffeine Pharmacokinetics

| Parameter[a] | Condition 3[b] | Condition 4[c] |
|---|---|---|
| $C_{max}$ (ng/mL) | 33.4 ± 9.5 | 37.4 ± 11.8 |
| $T_{max}$ (hours) | 0.8 (0.5-1.5) | 1.0 (0.3-1.5) |
| $t_{1/2}$ (hours) | 6.2 ± 3.8 | 5.5 ± 2.2 |
| AUC (hr*ng/mL/mg) | 262.0 ± 74.1 | 323 ± 209 |
| CL/F (L/hr) | 4.1 ± 1.1 | 4.3 ± 2.0 |
| Vd/F (L) | 33.5 ± 13.7 | 30.2 ± 12.4 |
| MRT (hours) | 8.4 ± 4.3 | 8.0 ± 3.2 |

[a]$T_{max}$ values are expressed as median (range). All other values are expressed as mean ± SD and represent dose-adjusted pharmacokinetic parameters.
[b]Caffeine 150 mg
[c]Theacrine 125 mg + Caffeine 150 mg

TABLE 3

Paraxanthine Pharmacokinetics

| Parameter[a] | Condition 3[b] | Condition 4[c] |
|---|---|---|
| $C_{max}$ (ng/mL) | 7.3 ± 1.5 | 8.4 ± 3.5 |
| $T_{max}$ (hours) | 5.0 (4.0-8.0) | 7.0 (1.5-8.0) |
| $t_{1/2}$ (hours) | 12.5 ± 12.7 | 14.8 ± 17.7 |
| AUC (hr*ng/mL/mg) | 174 ± 152 | 209 ± 202 |
| MRT (hours) | 19.1 ± 18.6 | 22.7 ± 26.2 |

Figure 12A:
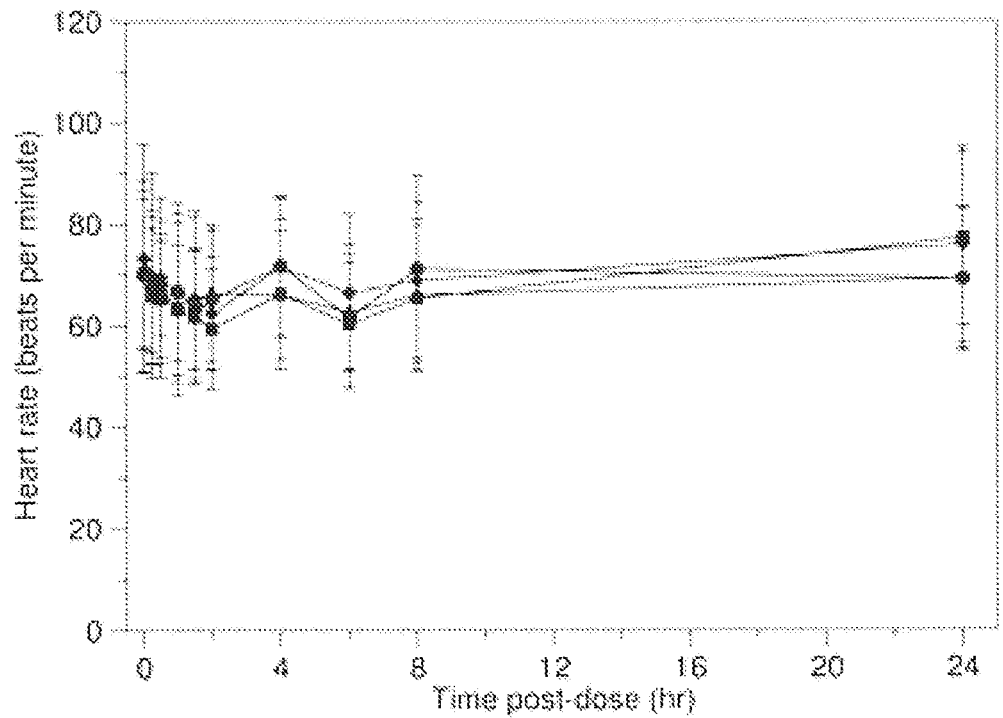
FIG. 12(A) depicts, in one embodiment, mean values in heart rate after single dose theacrine 25 mg (-●-), theacrine 125 mg (-■-), caffeine 150 mg (-♦-), or theacrine 125 mg plus caffeine 150 mg (-▲-).
Figure 12B:
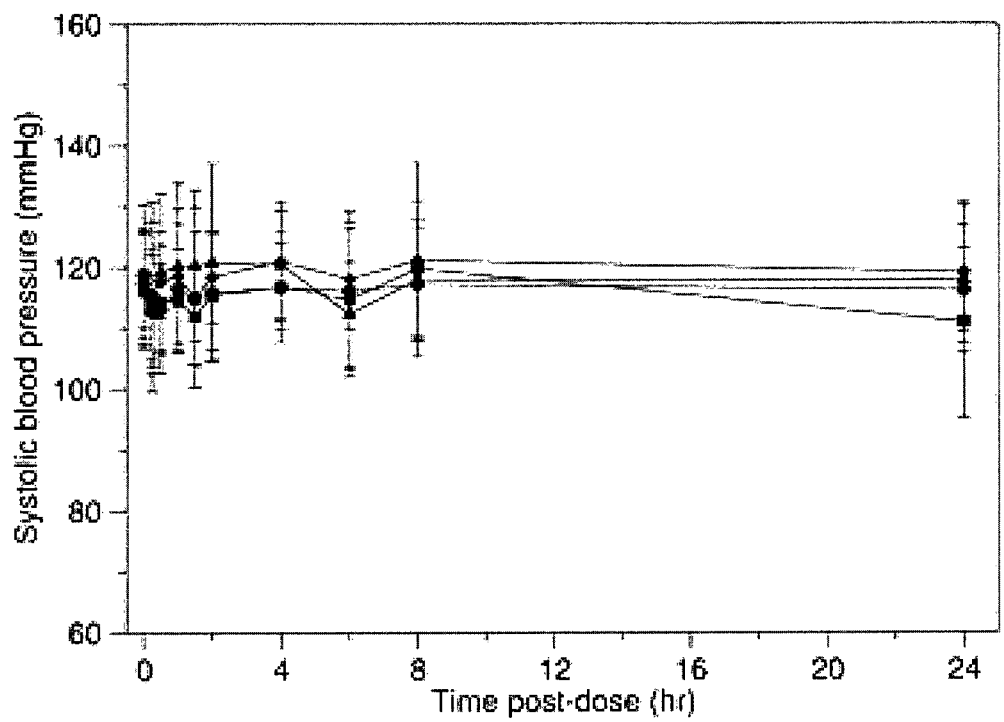
FIG. 12(B) depicts, in one embodiment, mean values in systolic blood pressure after single dose theacrine 25 mg (-●-), theacrine 125 mg (-■-), caffeine 150 mg (-♦-), or theacrine 125 mg plus caffeine 150 mg (-▲-).
Figure 12C:
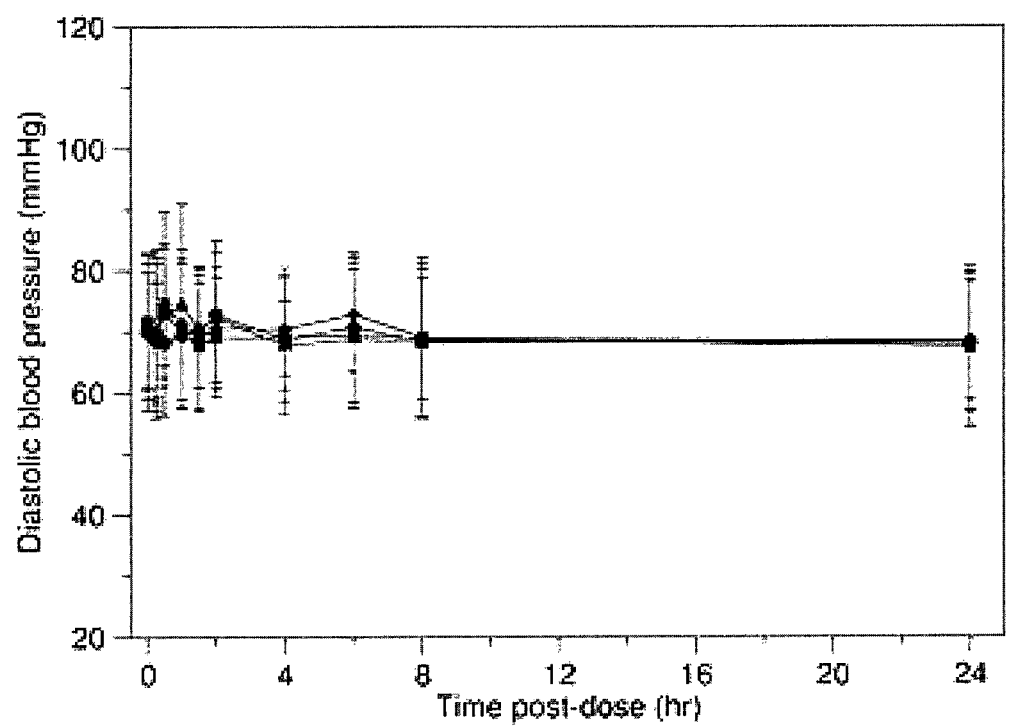
FIG. 12(C) depicts, in one embodiment, mean values in diastolic blood pressure after single dose theacrine 25 mg (-●-), theacrine 125 mg (-■-), caffeine 150 mg (-♦-), or theacrine 125 mg plus caffeine 150 mg (-▲-).
Figure 12D:
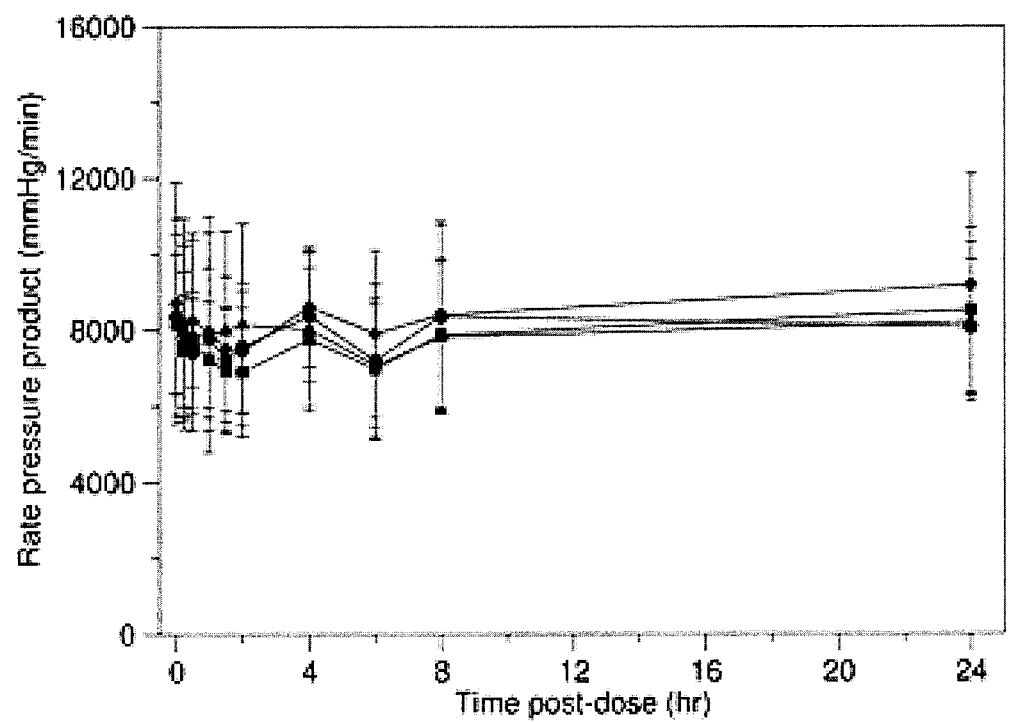
FIG. 12(D) depicts, in one embodiment, mean values in rate pressure product after single dose theacrine 25 mg (-●-), theacrine 125 mg (-■-), caffeine 150 mg (-♦-), or theacrine 125 mg plus caffeine 150 mg (-▲-).

[a]$T_{max}$ values are expressed as median (range). All other values are expressed as mean ± SD and represent dose-adjusted pharmacokinetic parameters.
[b]Caffeine 150 mg
[c]Theacrine 125 mg + Caffeine 150 mg Pharmacodynamics Hemodynamic parameters such as blood pressure and heart rate are elevated following co-administration of caffeine and other stimulants such as ephedrine. To determine the potential for a pharmacodynamics interaction between theacrine and caffeine, we evaluated systolic and diastolic blood pressure, heart rate, and rate pressure product following administration of both theacrine (25 mg and 125 mg) and caffeine (150 mg) alone and in combination (theacrine 125 mg plus caffeine 150 mg). Heart rate decreased slightly over the first two hours following administration for each of the four conditions returning to baseline by 24 hours post-ingestion (FIG. 12A). Systolic/diastolic blood pressure and rate pressure product remained relatively constant across the 24 hour evaluation period for each of the four conditions (FIGS. 12B, 12C, and 12D). For FIGS. 12A, 12B, 12C, and 12D, data are presented as mean±standard deviation. Single dose theacrine 25 mg (solid circle), theacrine 125 mg (solid square), caffeine 150 mg (solid diamond), theacrine 125 mg plus caffeine 150 mg (solid triangle).

The experimental results reveal that the pharmacokinetics of theacrine, when ingested alone, were similar between the two doses tested. However, following co-ingestion with caffeine, theacrine disposition was significantly altered. Specifically, caffeine decreased theacrine's oral clearance (CL/F), which correlated with enhanced theacrine exposure parameters, area under the plasma concentration time curve (AUC) and maximum concentration ($C_{max}$). It is impossible to determine with certainty the exact mechanism for enhanced theacrine exposure, viz., decreased CL and/or increased oral bioavailability (F), in the absence of intravenous data. However, the finding that theacrine's elimination half-life ($t_{1/2}$ or Vd/CL) was unaffected by caffeine indicates that caffeine enhances theacrine's oral bioavailability (F), which is also consistent with the decreased oral volume of distribution (Vd/F) of theacrine. Theacrine had no impact on the pharmacokinetics of caffeine or paraxanthine, which is the primary caffeine metabolite in humans formed via CYP1A2-mediated 3-N-demethylation. Caffeine is completely absorbed following oral administration. Such results indicate that theacrine would not have a reciprocal effect on caffeine bioavailability. Determination of whether or not theacrine is a CYP1A2 substrate will provide further insight into caffeine's effect on theacrine disposition, viz., enhanced fraction absorbed and/or reduced first-pass hepatic metabolism.

One study subject was found to have exaggerated theacrine exposure in all treatment arms. It is unclear, however, whether the finding is genetic and/or environmental. The presence of a 5-methyl substituent and a carbamide at the 6-position distinguish theacrine from caffeine. Because theacrine contains a 3-methyl substituent, the primary site of caffeine metabolism via CYP1A2-mediated demethylation, it is possible that theacrine is also susceptible to CYP1A2-mediated metabolism. Caffeine exposure ($AUC_{0-\infty}$) is controlled by both environmental, as well as genetic factors. In particular, the CYP1A2 polymorphism (r52470893), located in the common promoter region between CYPJA] and CYP1A2, significantly associated with caffeine exposure in non-smokers, but not in smokers. Non-smokers heterozygous or homozygous for the CYPJAI/CYP1A2 A allele had a significantly lower caffeine exposure compared to nullizygous individuals. Additional environmental factors including oral contraceptive use mask the effect of genetics on caffeine metabolism. The role of pharmacogenetics in theacrine pharmacokinetics and pharmacodynamics is of potential importance should CYP1A2 prove to be an important theacrine elimination pathway.

At the doses tested, the results reveal no effect on baseline hemodynamic parameters, e.g. heart rate and blood pressure, among the subjects receiving theacrine or caffeine administered alone or in combination. Such data are consistent with other studies demonstrating that theacrine supplementation (up to 400 mg/day for 8 weeks) appears to be safe in humans with no adverse effects on hemodynamic parameters. It is surprised to find that in repeat dose theacrine studies there is an absence of either sensitization or pharmacodynamic tolerance. Caffeine is a mixed $A_1/A_2$, adenosine receptor (AR) antagonist. It is believed that the acute psychostimulatory activity of caffeine is related to its ability to antagonize the $A_1$ AR, which removes inhibition of the $A_{2A}$ AR leading to NMDA-dependent release of glutamate and dopamine. Following chronic caffeine administration, however, caffeine's primary effects shift from $A_1$-dependent to $A_{2A}$-dependent antagonism in tolerant individuals due to $A_1$ AR desensitization. Administration of a cocktail containing both $A_1$ and $A_{2A}$ AR antagonists blocks theacrine stimulating activity in rats. However, simultaneous administration of $A_1$ and $A_{2A}$ AR antagonists prevents the determination of individual contribution of $A_1$ and $A_{2A}$ AR to the pharmacologic effects of theacrine. These data present a hypothesis that theacrine has different $A_1$ and $A_{2A}$ binding affinities than caffeine, which permits discrimination between the A1 and $A_{2A}$ receptors at physiologically relevant concentrations. Theacrine's preferential reliance on $A_{2A}$ AR antagonism would provide a mechanistic basis for lack of pharmacodynamic tolerance. Overall, the experimental data suggest that the interactions between theacrine and adenosine receptors are complex.

Example 3

Improvements in Subjective Feelings, Cognitive Performance, and Hemodynamics

In one clinical study, the effects of a single dose of theacrine, caffeine, or their combination on subjective feelings, cognitive performance, and hemodynamics in men and women were examined. In the study, 24 men and 26 women ingested a placebo, theacrine at 25 mg, theacrine at 125 mg, caffeine at 150 mg, or combination of 125 mg theacrine and 150 mg caffeine on five separate occasions, which were separated by approximately one week. Subjects rated their subjective feelings using a 10 cm visual analog scale at 30 minutes, 1, 2, 3, 4, and 5 hours post ingestion and performed the trail making test (TMT) of cognitive performance at baseline and at hours 2 and 4 post ingestion. Subjective feelings of attentiveness, sense of focus, and sense of energy improved with all active treatments. More favorable scores were generally associated with the caffeine and theacrine/caffeine combination treatments. Self-reported motivation to exercise significantly increased in caffeine and theacrine/caffeine combination treatments. Caffeine and theacrine/caffeine combination resulted in a significant increase in subjective focus from baseline to 2 hours post-ingestion, while the 125 mg theacrine treatment reached statistical significance at 3 hours post-ingestion. Motivation to exercise and sense of energy significantly increased from baseline to 2 hours post-ingestion in caffeine and theacrine/caffeine combination treatments. No condition effects were noted for the TMT ($p>0.05$), although a trend was present ($p=0.069$) for theacrine/caffeine combination treatment, with TMT time improved at 4 hours post ingestion compared to pre-ingestion. These findings indicate that theacrine, when used alone at 125 mg or in combination with caffeine, is safe and effective at improving subjective feelings related to energy in healthy men and women. Moreover, the data show that the combination of theacrine and caffeine may improve cognitive performance as assessed by the TMT.

Example 4

Improvements in Cognitive Performance

Another clinical study will demonstrate synergistic improvements in exercise performance and time to exhaustion obtained from 125 mg theacrine and 150 mg caffeine combination treatment over 275 mg caffeine or 275 theacrine administered alone. The purpose of this randomized, placebo-controlled, four-condition, double-blind clinical trial is to determine and compare the effects of theacrine to caffeine on various measures of cognitive performance under fatiguing conditions of a simulated athletic contest in high level male and female soccer players. Secondary purposes are to determine whether there is a synergistic effect of theacrine/caffeine combination as well as the impact on time-to-exhaustion in an "added time" scenario. After giving informed consent, 20 (males n=10, females n=10) Division I and professional soccer players will undergo baseline performance testing and then randomly assigned to order of supplementation of a placebo (P), caffeine (C), theacrine (T), and theacrine/caffeine combination (TC). In each condition, subjects will undergo a 15 minutes dynamic warm-up and then engage in a simulated soccer game on a high-speed treadmill. The "game" will be divided into two 45-minute halves. Simple, choice, and cognitive-load reaction time will be assessed immediately following each 45-minute half. After the second assessment, subjects will immediately be put back on the treadmill and asked to run to volitional fatigue at 90% VO2max. The experimental results indicated that 125 mg theacrine/150 mg caffeine combined treatment outperformed 275 mg pure caffeine or 275 mg pure theacrine interventions. At almost half of the pure caffeine or pure theacrine dose, the combined theacrine/caffeine treatment resulted in a true synergistic and superior performance in comparison to the pure caffeine, the pure theacrine, or placebo group. More specifically, the combination of 125 mg theacrine/150 mg caffeine outperformed all other groups, including 275 mg pure caffeine, 275 mg of pure theacrine, and placebo, in measures of cognitive flexibility, attention and task switching, complex-choice reaction time and information processing.

Routes of Administration

The compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of theacrine in the body of the patient in a controlled formulation, with systemic or local release of the drug to occur at a later time. For example, the drug may be localized in a depot for controlled release to the circulation.

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

Whereas, the present invention has been described in relation to certain embodiments thereof, and many details have been put forth in its illustration, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and system for carrying out the several purposes of the present invention. It is important, therefore, that the claims be regarded as including such equivalent constructions insofar as they do not depart from the spirit and scope of the present invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of formulating a dietary supplement comprising the step of:
    combining a nutraceutically acceptable carrier with theacrine, caffeine, and methylliberine;
    wherein the dietary supplement is formulated for oral administration;
    wherein the theacrine is present in the dietary supplement in an amount that is to modulate activity of the caffeine; and
    wherein the theacrine and caffeine are present in the dietary supplement in a ratio of about 0.5:1 to about 50:1 by weight caffeine:theacrine.

2. The method of claim 1, wherein the theacrine has a purity of at least 95%.

3. The method of claim 1, wherein the theacrine is present in the dietary supplement in an amount of from about 5 mg to about 850 mg.

4. The method of claim 1, wherein the dietary supplement is formulated into a solid oral dosage form.

5. The method of claim 4, wherein said solid oral dosage form is a powder, capsule, or tablet.

6. The method of claim 1, wherein the dietary supplement is formulated to, upon oral administration, increase mood, energy, focus, concentration, and/or sexual desire.

7. The method of claim 1, wherein the theacrine is produced synthetically or is isolated from a natural source and purified to at least 50% theacrine.

8. The method of claim 1, wherein said caffeine is present in the dietary supplement in an amount of about 25 mg to about 650 mg.

9. The method of claim 1, wherein the theacrine is present in the dietary supplement in an amount from about 65 mg to about 300 mg.

10. The method of claim 1, wherein the ratio is about 1:1 to about 10:1.

11. The method of claim 1, wherein the ratio is about 2:1 to about 4:1.

12. The method of claim 1, wherein the ratio is about 1.2:1.

13. A method of modulating activity of a stimulant comprising the steps of:
    providing a dietary supplement comprising a nutraceutically acceptable carrier in combination with theacrine, caffeine, and methylliberine, and
    administering the dietary supplement to a subject to modulate activity of the stimulant;
    wherein the dietary supplement is formulated for oral administration;
    wherein the stimulant is caffeine, and theacrine is included in the supplement in an amount that modulates activity of the caffeine;
    wherein the theacrine and caffeine are present in the dietary supplement in a ratio of about 0.5:1 to about 50:1 by weight caffeine:theacrine.

14. The method of claim 13, wherein the theacrine has a purity of at least 95%.

15. The method of claim 13, wherein the theacrine is present in the dietary supplement in an amount of from about 5 mg to about 850 mg.

16. The method of claim 13, wherein the dietary supplement is formulated into a solid oral dosage form.

17. The method of claim 16, wherein said solid oral dosage form is a powder, capsule, or tablet.

18. The method of claim 13, wherein the dietary supplement is formulated to, upon oral administration, increase mood, energy, focus, concentration, and/or sexual desire.

19. The method of claim 13, wherein the theacrine is produced synthetically or is isolated from a natural source and purified to at least 50% theacrine.

20. The method of claim 13, wherein said caffeine is present in the dietary supplement in an amount of about 25 mg to about 650 mg.

21. The method of claim 13, wherein the theacrine is present in the dietary supplement in an amount from about 65 mg to about 300 mg.

22. The method of claim 13, wherein the ratio is about 1:1 to about 10:1.

23. The method of claim 13, wherein the ratio is about 2:1 to about 4:1.

24. The method of claim 13, wherein the ratio is about 1.2:1.

\* \* \* \* \*